(12) United States Patent
Walovitch et al.

(10) Patent No.: US 8,012,457 B2
(45) Date of Patent: Sep. 6, 2011

(54) ULTRASOUND CONTRAST AGENT DOSAGE FORMULATION

(75) Inventors: Richard Walovitch, Framingham, MA (US); Howard Bernstein, Cambridge, MA (US); Donald Chickering, Framingham, MA (US); Julie Straub, Winchester, MA (US)

(73) Assignee: Acusphere, Inc., Lexington, MA (US)

( * ) Notice: Subject to any disclaimer, the term of this patent is extended or adjusted under 35 U.S.C. 154(b) by 199 days.

(21) Appl. No.: 11/143,170

(22) Filed: Jun. 2, 2005

(65) Prior Publication Data
US 2005/0271591 A1    Dec. 8, 2005

Related U.S. Application Data

(60) Provisional application No. 60/577,126, filed on Jun. 4, 2004.

(51) Int. Cl.
*A61B 8/00* (2006.01)
*A61K 49/00* (2006.01)

(52) U.S. Cl. ......... 424/9.1; 424/9.5; 424/9.51; 424/9.52

(58) Field of Classification Search ........... 424/9.5–9.52
See application file for complete search history.

(56) References Cited

U.S. PATENT DOCUMENTS

| | | |
|---|---|---|
| 3,044,942 A | 7/1962 | Babtist |
| 3,429,827 A | 2/1969 | Ruus |
| 3,615,972 A | 10/1971 | Morehouse, Jr. et al. |
| 3,650,831 A | 3/1972 | Jungermann et al. |
| 3,663,687 A | 5/1972 | Evans |
| 3,968,203 A | 7/1976 | Spitzer et al. |
| 4,027,007 A | 5/1977 | Messina |
| 4,089,800 A | 5/1978 | Temple |
| 4,127,622 A | 11/1978 | Wantanabe et al. |
| 4,173,488 A | 11/1979 | Vassiliades et al. |
| 4,177,177 A | 12/1979 | Vanderhoff et al. |
| 4,180,593 A | 12/1979 | Cohan |
| 4,247,406 A | 1/1981 | Widder et al. |
| 4,265,251 A | 5/1981 | Tickner |
| 4,276,885 A | 7/1981 | Tickner et al. |
| 4,331,654 A | 5/1982 | Morris |
| 4,442,843 A | 4/1984 | Rasor et al. |
| 4,450,150 A | 5/1984 | Sidman |
| 4,452,773 A | 6/1984 | Molday |
| 4,466,442 A | 8/1984 | Hilmann et al. |
| 4,490,407 A | 12/1984 | Lafon |
| 4,501,726 A | 2/1985 | Schroder et al. |
| 4,533,254 A | 8/1985 | Cooke et al. |
| 4,544,545 A | 10/1985 | Ryan et al. |
| 4,572,203 A | 2/1986 | Feinstein |
| 4,572,869 A | 2/1986 | Wismer et al. |
| 4,637,905 A | 1/1987 | Gardner et al. |
| 4,657,756 A | 4/1987 | Rasor et al. |
| 4,675,173 A | 6/1987 | Widder |
| 4,681,119 A | 7/1987 | Rasor et al. |
| 4,684,479 A | 8/1987 | D'Arrigo |
| 4,692,325 A | 9/1987 | Kritzler |
| 4,718,433 A | 1/1988 | Feinstein |
| 4,731,239 A | 3/1988 | Gordon |
| 4,757,128 A | 7/1988 | Domb et al. |
| 4,767,610 A | 8/1988 | Long |
| 4,774,958 A | 10/1988 | Feinstein |
| 4,789,724 A | 12/1988 | Domb et al. |
| 4,832,941 A | 5/1989 | Berwing et al. |
| 4,844,882 A | 7/1989 | Widder et al. |
| 4,857,311 A | 8/1989 | Domb et al. |
| 4,859,363 A | 8/1989 | Davis et al. |
| 4,863,715 A | 9/1989 | Jacobsen et al. |
| 4,865,836 A | 9/1989 | Long |
| 4,888,176 A | 12/1989 | Langer et al. |
| 4,895,876 A | 1/1990 | Schweighardt et al. |
| 4,900,540 A | 2/1990 | Ryan et al. |
| 4,904,479 A | 2/1990 | Illum |
| 4,913,908 A | 4/1990 | Couvreur et al. |
| 4,927,623 A | 5/1990 | Long, Jr. |

(Continued)

FOREIGN PATENT DOCUMENTS

| | | |
|---|---|---|
| AU | 70982/91 | 10/1991 |
| AU | 7614491 | 11/1991 |
| AU | 33900 89 | 8/1992 |
| AU | 635200 | 3/1993 |
| CA | 2036107 | 8/1991 |
| CA | 2273140 | 4/1993 |
| CA | 2085525 | 7/1993 |
| CA | 1336164 | 7/1995 |
| DE | 4 100 470 | 3/1925 |
| DE | 3 246 386 | 6/1984 |

(Continued)

OTHER PUBLICATIONS

Echocardiography (Wikipedia).*
Levene, et al., "Characterization of Albunex™" *J. Accoust. Soc. Am.*, 87(Suppl.1):S69-S70 (1990).
Mittl, "Perfluorocarbon gases in the suprachordial space of rabbit eyes" *Graefe's Arch. Clin, Exp. Ophthal*, 228(6):589-93 (1990).

(Continued)

*Primary Examiner* — Michael G Hartley
*Assistant Examiner* — Melissa Perreira
(74) *Attorney, Agent, or Firm* — Pabst Patent Group LLP

(57) ABSTRACT

Clinical studies have been conducted and specific dosage formulations developed using polymeric microparticles having incorporated therein perfluorocarbon gases that provide significantly enhanced images of long duration. The dosage formulation includes microparticles formed of a biocompatible polymer, preferably including a lipid incorporated therein, and containing a perfluorocarbon that is a gas at body temperature. The microparticles are provided to a patient in an amount effective to enhance ultrasound imaging in the ventricular chambers for more than 5 minutes or in the myocardium for more than a minute, in a dose ranging from 0.025 to 8.0 mg microparticles/kg body weight. Preferably the dose ranges from 0.05 to 4.0 mg microparticles/kg body weight. The dosage formulation typically is provided in a vial. A typical formulation is in the form of a dry powder that is reconstituted with sterile water prior to use by adding the water to the vial or syringe of the dry powder and shaking to yield an isosmotic or isotonic suspension of microparticles.

19 Claims, No Drawings

U.S. PATENT DOCUMENTS

| | | |
|---|---|---|
| 4,957,656 A | 9/1990 | Cerny et al. |
| 4,978,483 A | 12/1990 | Redding, Jr. |
| 4,985,550 A | 1/1991 | Charpoit et al. |
| 4,987,154 A | 1/1991 | Long |
| 4,993,415 A | 2/1991 | Long |
| 5,049,322 A | 9/1991 | Devissaguet et al. |
| 5,077,036 A | 12/1991 | Long |
| 5,078,146 A | 1/1992 | Sato |
| 5,080,885 A | 1/1992 | Long |
| 5,088,499 A | 2/1992 | Unger |
| 5,107,842 A | 4/1992 | Levine et al. |
| 5,114,703 A | 5/1992 | Wolf et al. |
| 5,117,830 A * | 6/1992 | McAfee et al. ............... 600/431 |
| 5,123,414 A | 6/1992 | Unger |
| 5,127,405 A | 7/1992 | Alcala et al. |
| 5,137,928 A | 8/1992 | Erbel et al. |
| 5,141,738 A | 8/1992 | Rasor et al. |
| 5,145,684 A | 9/1992 | Liversidge et al. |
| 5,147,631 A | 9/1992 | Glajch et al. |
| 5,149,319 A | 9/1992 | Unger |
| 5,155,215 A | 10/1992 | Ramney |
| 5,171,755 A | 12/1992 | Kakufman |
| 5,179,955 A | 1/1993 | Leven et al. |
| 5,205,290 A | 4/1993 | Unger |
| 5,209,720 A | 5/1993 | Unger |
| 5,228,446 A | 7/1993 | Unger |
| 5,230,882 A | 7/1993 | Unger |
| 5,260,496 A | 11/1993 | Meinert et al. |
| 5,271,928 A | 12/1993 | Schneider et al. |
| 5,271,961 A | 12/1993 | Mathiowitz et al. |
| 5,281,408 A | 1/1994 | Unger |
| 5,284,645 A | 2/1994 | Long |
| 5,315,997 A | 5/1994 | Widder et al. |
| 5,334,381 A | 8/1994 | Unger |
| 5,344,393 A | 9/1994 | Roth |
| 5,348,016 A | 9/1994 | Unger et al. |
| 5,350,571 A | 9/1994 | Kaufman et al. |
| 5,352,435 A | 10/1994 | Unger |
| 5,354,549 A | 10/1994 | Klaveness et al. |
| 5,362,478 A | 11/1994 | Desai et al. |
| 5,380,519 A | 1/1995 | Schneider et al. |
| 5,393,524 A | 2/1995 | Quay |
| 5,406,950 A | 4/1995 | Brandenburger et al. |
| 5,409,688 A | 4/1995 | Quay |
| 5,413,774 A | 5/1995 | Schneider et al. |
| 5,425,366 A | 6/1995 | Reinhardt et al. |
| 5,445,813 A * | 8/1995 | Schneider et al. ........... 424/9.51 |
| 5,456,900 A | 10/1995 | Unger |
| 5,456,901 A | 10/1995 | Unger |
| 5,469,854 A | 11/1995 | Unger et al. |
| 5,496,535 A | 3/1996 | Kirkland |
| 5,498,421 A | 3/1996 | Grinstaff et al. |
| 5,501,863 A | 3/1996 | Rossling et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,518,709 A | 5/1996 | Sutton et al. |
| 5,527,521 A | 6/1996 | Unger |
| 5,529,766 A | 6/1996 | Klaveness et al. |
| 5,531,980 A | 7/1996 | Schneider et al. |
| 5,536,489 A | 7/1996 | Lohrmann et al. |
| 5,536,490 A | 7/1996 | Klaveness et al. |
| 5,542,935 A | 8/1996 | Unger et al. |
| 5,547,656 A | 8/1996 | Unger |
| 5,552,133 A | 9/1996 | Lambert et al. |
| 5,556,610 A | 9/1996 | Yan et al. |
| 5,558,094 A | 9/1996 | Quay |
| 5,558,854 A | 9/1996 | Quay |
| 5,558,856 A | 9/1996 | Klaveness et al. |
| 5,558,857 A | 9/1996 | Klaveness et al. |
| 5,559,266 A | 9/1996 | Klaveness et al. |
| 5,560,364 A * | 10/1996 | Porter ............................ 600/458 |
| 5,562,893 A | 10/1996 | Lohrmann |
| 5,565,215 A | 10/1996 | Gref et al. |
| 5,567,413 A | 10/1996 | Klaveness et al. |
| 5,567,415 A | 10/1996 | Porter |
| 5,573,751 A | 11/1996 | Quay |
| 5,578,291 A | 11/1996 | Porter |
| 5,578,292 A | 11/1996 | Schneider et al. |
| 5,585,112 A | 12/1996 | Unger et al. |
| 5,597,549 A | 1/1997 | Schneider et al. |
| 5,605,673 A | 2/1997 | Schutt et al. |
| 5,611,344 A | 3/1997 | Bernstein et al. |
| 5,614,169 A | 3/1997 | Klaveness et al. |
| 5,618,514 A | 4/1997 | Schroder et al. |
| 5,626,833 A | 5/1997 | Schutt et al. |
| 5,637,289 A | 6/1997 | Klaveness et al. |
| 5,637,564 A | 6/1997 | Pavia et al. |
| 5,639,442 A | 6/1997 | Unger et al. |
| 5,639,443 A | 6/1997 | Schutt et al. |
| 5,639,473 A | 6/1997 | Grinstaff et al. |
| 5,643,553 A | 7/1997 | Schneider et al. |
| 5,648,062 A | 7/1997 | Klaveness et al. |
| 5,653,959 A | 8/1997 | Tournier et al. |
| 5,658,551 A | 8/1997 | Schneider et al. |
| 5,670,135 A | 9/1997 | Schroder |
| 5,674,468 A | 10/1997 | Klaveness et al. |
| 5,676,925 A | 10/1997 | Klaveness et al. |
| 5,685,310 A | 11/1997 | Porter |
| 5,686,060 A | 11/1997 | Schneider et al. |
| 5,688,490 A | 11/1997 | Tournier et al. |
| 5,693,321 A | 12/1997 | Klaveness et al. |
| 5,695,741 A | 12/1997 | Schutt et al. |
| 5,701,899 A | 12/1997 | Porter |
| 5,705,187 A | 1/1998 | Unger |
| 5,711,933 A | 1/1998 | Bichon |
| 5,714,528 A | 2/1998 | Unger et al. |
| 5,714,529 A | 2/1998 | Unger et al. |
| 5,716,597 A | 2/1998 | Lohrmann et al. |
| 5,718,884 A | 2/1998 | Klaveness et al. |
| 5,720,938 A | 2/1998 | Schutt et al. |
| 5,730,954 A | 3/1998 | Albayrak et al. |
| 5,730,955 A | 3/1998 | Lohrmann |
| 5,733,572 A | 3/1998 | Unger et al. |
| 5,740,807 A | 4/1998 | Porter |
| 5,798,091 A | 8/1998 | Trevino et al. |
| 5,804,162 A | 9/1998 | Kalbanov et al. |
| 5,827,504 A | 10/1998 | Yan et al. |
| 5,830,435 A | 11/1998 | Yan et al. |
| 5,837,221 A * | 11/1998 | Bernstein et al. ............ 424/9.52 |
| 5,840,275 A | 11/1998 | Bichon et al. |
| 5,846,518 A | 12/1998 | Yan et al. |
| 5,853,698 A | 12/1998 | Straub et al. |
| 5,863,520 A | 1/1999 | Bichon et al. |
| 5,908,610 A | 6/1999 | Schneider et al. |
| 5,911,972 A | 6/1999 | Schneider et al. |
| 5,955,143 A | 9/1999 | Wheatley |
| 5,961,956 A | 10/1999 | Yan et al. |
| 5,980,937 A | 11/1999 | Tournier et al. |
| 6,019,960 A | 2/2000 | Schutt |
| 6,045,777 A | 4/2000 | Church et al. |
| 6,056,943 A | 5/2000 | Schutt |
| 6,110,443 A | 8/2000 | Schneider et al. |
| 6,123,922 A | 9/2000 | Bichon et al. |
| 6,132,699 A | 10/2000 | Bernstein et al. |
| 6,139,818 A | 10/2000 | Bichon et al. |
| 6,146,657 A | 11/2000 | Unger et al. |
| 6,177,062 B1 | 1/2001 | Stein et al. |
| 6,183,725 B1 | 2/2001 | Yan et al. |
| 6,187,288 B1 | 2/2001 | Schneider et al. |
| 6,200,548 B1 | 3/2001 | Bichon et al. |
| 6,258,339 B1 | 7/2001 | Schutt et al. |
| 6,258,378 B1 * | 7/2001 | Schneider et al. ............ 424/450 |
| 6,280,704 B1 | 8/2001 | Schutt et al. |
| 6,333,021 B1 | 12/2001 | Schneider et al. |
| 6,372,195 B1 | 4/2002 | Schutt et al. |
| 6,403,057 B1 | 6/2002 | Schneider et al. |
| 6,416,740 B1 | 7/2002 | Unger |
| 6,479,034 B1 | 11/2002 | Unger et al. |
| 6,528,039 B2 | 3/2003 | Unger |
| 6,592,846 B1 | 7/2003 | Schneider et al. |
| 6,613,306 B1 | 9/2003 | Schneider et al. |
| 6,723,303 B1 | 4/2004 | Quay |
| 6,773,696 B2 | 8/2004 | Unger |
| 6,811,766 B1 | 11/2004 | Eriksen et al. |
| 6,875,420 B1 | 4/2005 | Quay |
| 6,881,397 B2 | 4/2005 | Schneider et al. |

| | | | |
|---|---|---|---|
| 6,896,659 | B2 | 5/2005 | Conston et al. |
| 6,896,875 | B2 | 5/2005 | Schneider et al. |
| 2005/0118104 | A1 | 6/2005 | Ostensen et al. |

FOREIGN PATENT DOCUMENTS

| | | |
|---|---|---|
| DE | 3 341 001 | 5/1985 |
| DE | 35 29 195 | 2/1987 |
| DE | 3 713 326 | 10/1987 |
| DE | 38 03 972 | 8/1989 |
| DE | 4 127 442 | 2/1993 |
| DE | 195 10 690 | 9/1996 |
| EP | 0 077 752 | 4/1983 |
| EP | 0 092 918 | 11/1983 |
| EP | 0 122 624 | 10/1984 |
| EP | 0 123 235 | 10/1984 |
| EP | 0 166 596 | 1/1986 |
| EP | 0 212 568 | 3/1987 |
| EP | 0 224 934 | 6/1987 |
| EP | 0 231 091 | 8/1987 |
| EP | 0 245 019 | 11/1987 |
| EP | 0 295 055 | 12/1988 |
| EP | 0 307 087 | 3/1989 |
| EP | 0 322 350 | 6/1989 |
| EP | 0 324 938 | 7/1989 |
| EP | 0 327 490 | 8/1989 |
| EP | 0 357 163 | 3/1990 |
| EP | 0 359 246 | 3/1990 |
| EP | 0 365 467 | 4/1990 |
| EP | 0 398 935 | 11/1990 |
| EP | 0 441 468 | 8/1991 |
| EP | 0 454 044 | 10/1991 |
| EP | 0 458 079 | 11/1991 |
| EP | 0 458 745 | 11/1991 |
| EP | 0 467 031 | 1/1992 |
| EP | 0 502 814 | 9/1992 |
| EP | 0 512 693 | 11/1992 |
| EP | 0 520 888 | 12/1992 |
| EP | 0 520 889 | 12/1992 |
| EP | 0 535 387 | 4/1993 |
| EP | 0 552 802 | 7/1993 |
| EP | 0 554 213 | 8/1993 |
| EP | 0 576 519 | 1/1994 |
| EP | 0 576 521 | 1/1994 |
| EP | 0 605 477 | 7/1994 |
| EP | 0 619 743 | 10/1994 |
| EP | 0 644 777 | 3/1995 |
| EP | 0 681 843 | 11/1995 |
| EP | 0 711 179 | 5/1996 |
| EP | 0 744 961 | 12/1996 |
| EP | 0 804 932 | 11/1997 |
| EP | 0 904 113 | 3/1999 |
| EP | 0 957 942 | 11/1999 |
| EP | 1 019 022 | 7/2000 |
| FR | 2 596 399 | 10/1987 |
| GB | 1044680 | 10/1966 |
| GB | 1265615 | 3/1972 |
| GB | 2105189 | 3/1983 |
| JP | 59-067229 | 4/1984 |
| JP | 63-060943 | 3/1988 |
| JP | 2084401 | 3/1990 |
| JP | 2196730 | 8/1990 |
| JP | 10-505900 | 6/1998 |
| WO | WO80/02365 | 11/1980 |
| WO | WO 83/01738 | 5/1983 |
| WO | WO 83/03426 | 10/1983 |
| WO | WO 84/02643 | 7/1984 |
| WO | WO 84/02838 | 8/1984 |
| WO | WO 85/02772 | 7/1985 |
| WO | WO89/06978 | 8/1989 |
| WO | WO89/10118 | 11/1989 |
| WO | WO90/01952 | 3/1990 |
| WO | WO90/07491 | 7/1990 |
| WO | WO91/09629 | 7/1991 |
| WO | WO91/12823 | 9/1991 |
| WO | WO91/15244 | 10/1991 |
| WO | WO91/18612 | 12/1991 |
| WO | WO92/02560 | 2/1992 |
| WO | WO92/05806 | 4/1992 |
| WO | WO92/08496 | 5/1992 |
| WO | WO92/11873 | 7/1992 |
| WO | WO92/15284 | 9/1992 |
| WO | WO92/17212 | 10/1992 |
| WO | WO92/17213 | 10/1992 |
| WO | WO92/17514 | 10/1992 |
| WO | WO 92/18164 | 10/1992 |
| WO | WO92/18165 | 10/1992 |
| WO | WO92/18169 | 10/1992 |
| WO | WO 92/19272 | 11/1992 |
| WO | WO92/21382 | 12/1992 |
| WO | WO92/22247 | 12/1992 |
| WO | WO92/22298 | 12/1992 |
| WO | WO 93/00933 | 1/1993 |
| WO | WO93/01798 | 2/1993 |
| WO | WO 93/01806 | 2/1993 |
| WO | WO 93/05819 | 4/1993 |
| WO | WO93/06869 | 4/1993 |
| WO | WO93/07905 | 4/1993 |
| WO | WO 93/10440 | 5/1993 |
| WO | WO 93/13802 | 7/1993 |
| WO | WO 93/13808 | 7/1993 |
| WO | WO 93/13809 | 7/1993 |
| WO | WO93/17718 | 9/1993 |
| WO | WO 93/25242 | 12/1993 |
| WO | WO 94/02122 | 2/1994 |
| WO | WO 94/06477 | 3/1994 |
| WO | WO 94/07514 | 4/1994 |
| WO | WO 94/08627 | 4/1994 |
| WO | WO 94/09625 | 5/1994 |
| WO | WO94/09829 | 5/1994 |
| WO | WO 94/16739 | 8/1994 |
| WO | WO94/19101 | 9/1994 |
| WO | WO94/21301 | 9/1994 |
| WO | WO94/21302 | 9/1994 |
| WO | WO94/21303 | 9/1994 |
| WO | WO94/28939 | 12/1994 |
| WO | WO95/01187 | 1/1995 |
| WO | WO 95/01324 | 1/1995 |
| WO | WO 95/03356 | 2/1995 |
| WO | WO 95/03357 | 2/1995 |
| WO | WO 95/06518 | 3/1995 |
| WO | WO 95/23615 | 9/1995 |
| WO | WO 95/24184 | 9/1995 |
| WO | WO 95/32006 | 11/1995 |
| WO | WO 96/03116 | 2/1996 |
| WO | WO 96/04018 | 2/1996 |
| WO | WO96/08234 | 3/1996 |
| WO | WO 96/15815 | 5/1996 |
| WO | WO 96/18420 | 6/1996 |
| WO | WO 96/26746 | 9/1996 |
| WO | WO 96/28191 | 9/1996 |
| WO | WO 96/32149 | 10/1996 |
| WO | WO 96/36314 | 11/1996 |
| WO | WO 96/38181 | 12/1996 |
| WO | WO 96/40275 | 12/1996 |
| WO | WO 96/40277 | 12/1996 |
| WO | WO 9640285 A1 * | 12/1996 |
| WO | WO 97/13503 | 4/1997 |
| WO | WO 97/22409 | 6/1997 |
| WO | WO 97/32609 | 9/1997 |
| WO | WO 97/41833 | 11/1997 |
| WO | WO 97/44013 | 11/1997 |
| WO | WO 97/46264 | 12/1997 |
| WO | WO 98/04292 | 2/1998 |
| WO | WO 98/29096 | 7/1998 |
| WO | WO 98/31346 | 7/1998 |
| WO | WO 98/51282 | 11/1998 |
| WO | WO 99/00149 | 1/1999 |
| WO | WO 01/07107 | 2/2001 |
| ZA | 89/0873 | 10/1989 |

OTHER PUBLICATIONS

Yang, et al, "Computed Tomographic Liver Enhancement with Poly(d,l-Lactide)-Microencapsulated Contrast Media," *Investigative Radiology* 29:S267-S270 (1994).

Church, "An In Vitro Study of the Acoustical Responses of AI-700" *The Fourth Heart Centre European Symposium on Ultrasound Contrast Imaging*, Jan. 21-22, 1999.

Church, "The Acoustical Responses of AI-700 In Vitro" *J. Am. Soc. Echocard.*, 13(5): 457 201B (2000).

Di Spirito, et al., "The Pharmacokinetics of a Perfluorocarbon Gas—An Echocardiographic Contrast Agent (AI-700)" *AAPS PharmSci.*, 5(S1) (2003).

Fetterman, et al., "Simultaneous Visualization of Perfusion and Wall Motion Abnormalities Using a New Selective Color Encoding Algorithm: Contrast Echo Studies With Agent AI-700" *J. Am. Soc. Echocard.*, 12(5):365 101S (1999).

Goldberg, et al, "Radio-frequency-induced Coagulation Necrosis in Rabbits: Immediate Detection at US with Synthetic Microsphere Contrast Agent" *Radiology*, 213(2): 438-444 (1999).

Grayburn, at al., "Comparison of AI-700 Echo and Nuclear Perfusion Imaging to Coronary Angiography in Patients with Suspected Coronary Disease" *J. Am. Soc. Echocard.*, 17(5): Abstract 502 (May 2004).

Picard, et al., "The Effects of AI-700 Echo-Contrast Perfusion and/or Wall Motion Imaging on Detection of Perfusion Defects in Patients With Coronary Artery Disease" *J. Am. Soc. Echocard.*, 14(5): 460 P3-2 (2001).

Walovitch, et al., "Initial Safety and Myocardial Perfusion Imaging Results With AI-700: A Synthetic Polymeric Ultrasound Contrast Agent" *J. Am. Soc. Echocard.*, 13(5): Abstract 457 (2000).

Weissman, et al., "Comparison of Myocardial Contrast Echo to $^{99m}$tc MIBI Spect In Patients With Myocardial Perfusion Defects: A Phase 2 Study of AI-700" *J. Am. Soc. Echocard.*, 14(5): 461 P3-4 (2001).

Weissman, et al., "Chronotropic Response After Dipyridamole Correlates with Increased AI-700 Echo and Nuclear Perfusion Sensitivity in Patients Screened for Coronary Disease" *J. Am. Soc. Echocard.*, 17(5): Abstracts 515 (May 2004).

Yao, et al., "AI-700, a New Ultrasound Contrast Agent Allows Reliable Detection of Hyperfused Zones in Acute Ischemia and Infarction not Only in Triggered Mode but Also in Continuous Imaging Mode" *J. Am. Coll. Cardiol.*, 33(2) Suppl.1, 466A (1999).

Yao, et al., "Hypoperfused Myocardial Mass Estimated from 3-Dimensional Contrast Echocardiography Using a Novel Contrast Agent, AI-700, Aids in Accurate Quantitation of Infarct Mass" *J. Am. Coll. Cardiol.*, 33(2) Suppl.1, 467A (1999).

Yao, at al., "Polar Map Display and Quantitation of Myocardial Area at Risk During Acute Coronary Occlusion from 3-D Contrast Echo: Comparison to 3-D Nuclear Quantitation" *Circulation, Suppl I*, 100(18): 361 (1999).

Yao, "Myocardial Perfusion Imaging Using AI-700" *The Eleventh European Symposium on Ultrasound Contrast Imaging*, (Jan. 24-25, 2002).

Yao, at al, "Evaluation of a New Ultrasound Contrast Agent (AI-700) Using Two-Dimensional and Three-Dimensional Imaging During Acute ischemia" *J. Am. Soc. Echocard.*, 15(7): 686-694 (2002).

Albunex Manufacturing Information, Mallinckrodt Medical, Inc. St. Louis, MO (1995).

Allen & Hansen, "Pharmacokinetics of Stealth Versus Conventional Liposomes: Effect of Dose" *Biochimica et Biophysics Acta* 1068:133-141 (1991).

Allen, et al., "Liposomes Containing Synthetic Lipid Derivatives of Poly(ethylene glycol) Show Prolonged Circulation Half-Lives in Vivo" *Biochimica et Biophysica Acta* 1066:29-36 (1991).

American Heart Assoication, *Abstracts of the 58th Scientific Sessions, Circulation* 72: Oct. 1985 III-427.

Barnhart, "Characteristics of Albunex: air-filled albumin microspheres for echocardiography contrast enhancement" *Invest. Radiol.* 25:162-164 (1990).

Beck, et al., "A New Long-Acting Injectable Microcapsule System for the Administration of Progesterone" *Fertility and Sterility* 31(5):545-551 (1979).

Benita, et al., "Characterization of Drug-Loaded Poly(d,l-lactide) Microspheres" *J. Pharmaceutical Sciences* 73(12):1721-1724 (1984).

Beppu, et al., "Prolonged myocardial contrast echocardiography via peripheral venous administration of QW3600 injection (EchoGen®): Its efficacy and side effects" *J. Am. Soc. Echocard.* 10:11-24 (1997).

Bleeker, H., et al., "On The Application of Ultrasonic Contrast Agents for Blood Fowmetry and Assessment of Cardiac Perfusion" *Journal of Ultrasound in Medicine*, 9:461-471 (1990).

Bleeker, H., et al., "Ultrasonic Characterization of Albunex®, a New Contrast Agent" *Journal Accoustical Society of America*, 87:1792-1797 (1990).

Bommer WJ, et al., "The safety of contrast echocardiography: Report of the committee on contrast echocardiography for the American Society of Echocardiography" *J Am. Coll Echo* 3(1):6-13 (1984).

Burns, "Mezzi Di Contrasto Per Ecografia Nella Diagnostic Radiologic" *La Radiologic Medica-Radiol Med.* 87(Supple, 1 al, n 5):71-82 (1994).

Butler, "Production of microbubbles for use as echo contrast agents" *J. Clin. Ultrasound* 14:408-412 (1986).

Carroll, et al., "Gelatin Encapsulated Nitrogen Microbubbles As Ultrasonic Contrast Agents" *Invest. Radiol.* 15(3):260-266 (1980).

Carroll, et al., "Ultrasonic Contrast Enhancement Of Tissue By Encapsulated Microbubbles" *Radiology* 143:747-750 (1982).

Carslaw and Jaeger, eds., *Conduction of heat in solids*, pp. 233-237 and pp. 351-352, Clarendon Press: London (1959).

Chang et al., "Perfluorocarbon gases in vitreous surgery" *Ophthalmology* 92(5):651-6 (1985).

Church, "The effects of an elastic solid surface layer on the radial pulsations of gas bubbles" *J. Acoustical Soc. Amer.* 97(3):1510-1521 (1995).

Commander, et al., "Linear pressure waves in bubbly liquids: Comparison between theory and experiments" *J. Scoust. Soc. Amer.* 85(2):732-746 (1989).

Constable, "Perfluoropentane in experimental ocular surgery" *Invest. Ophthalmol.* 13(8):627-9 (1974).

Davis, P. L., et al., "Echogenicity cause by stable microbubbles in a protein-lipid emulsion" *The Journal of Clinical Ultrasound* 9:249-252 (1981).

De Jong, N., et al., "Principles and Recent Developments in Ultrasound Contrast Agents" *Ultrasonics* 29:324-330 (1991).

De Jong, N., et al., "Absorption and scatter of encapsulated gas filled microspheres: theoretical considerations and some measurements" *Ultrasonics* 30:95-103 (1992).

De Jong, "Quantification of transpulmonary echocontrast effects" *Ultrasound in Med. & Biol.* 19(4):279-288 (1993).

De Jong & Cate, "New Ultrasound Contrast Agents and Technological Innovations," *Ultrasonics* 34(2-5):587-590 (1996).

Deng, et al., "Synthesis And Characterization Of Block Copolymers From D,L-Lactide And Poly(Ethylene Glycol) With Stannous Chloride" *J. Of Polymer Science: Part C: Polymer Letters* 28:411-416 (1990).

Dupont Technical Bulletin, "Freon: Technical Bulletin" pp. 1-8 (1964).

Dupont Technical Bulletin, "Freon Fluorocarbons: Properties and Applications" pp. 1-10 (1987).

Edwards, et al., "Large porous particles for pulmonary drug delivery" *Science* 276:1868-1871 (1997).

Edwards and Jarzynski, "Scattering of focused ultrasound by spherical microparticles" *J. Acoust. Soc. Am.* 74(3):100601012 (1983).

Eger, et al., "Molecular properties of the "ideal" inhaled anesthetic: Studies of fluorinated methanes, ethanes, propanes, and butanes" *Anesth. Analg.* 79:245-251 (1994).

Epstein, P., et al., "On the Stability of Gas Bubbles in Liquid-Gas Soultions" *Journal of Chemical Physics* 18:1505-1509, Nov. 1950.

Farnand, et al., "Preparation of hollow spherical articles" *Powder Technol.* 22:11-16 (1979).

Feinstein, S., et al., "Myocardial contrast echocardiography: examination of infracoronary injections, microbubble diameters and video intensity decay" *American Journal of Physilogic Imaging* 1:12-18 (1986).

Feinstein, "Myocardial perfusion imaging: contrast echocardiography today and tomorrow" *J. of the Amer. Coll. Of Cardiol.* 8:251-253 (1986).

Feinstein, et al., "Contrast Echocardiography During Coronary Arteriography in Humans: Perfusion and Anatomic Studies" *J. Am. Coll. Cardiol.* 11:59-65 (1988).

Feinstein, S., et al., "Safety and efficacy of a new transpulmonary ultrasound contrast agent: initial multicenter clinical results" *Journal of American College of Cardiology* 16:316-324 (1990).

Flament et al., Particularites de l'examen echographique après utilisation de gaz expansif dans la chirurgie du decollement de la retine. Extude experimentale et clinique. *Bull. Soc. Ophthal. France* 10(LXXXVIII):1183-8 (1988), abstract.

Fluery, "Le C3F8 dans le traitement des decollements de la retine associes a une proliferation vitreoretinienne" *J. Fr. Ophthalmol.* 12(2):89-94 (1989), abstract.

Fobbe, V. F., et al., "Farbkodierte duplexsonographie un ultraschallkontrastmittel-nachweis von renalen perfusionsdefekten im tierexperiment" *Fortschr. Rontgenstr.* 154:242-245 (1991). Abstract Only.

Foulks et al., "The Effect of Perfluoropropane on the Cornea in Rabbits and Cats", *Arch. Ophthalmol.* 105:256-259 (1987).

Fritzsch, et al., "Preclinical and Clinical Results With An Ultrasonic Agent" *Invest. Radiol.* 23(Suppl 1):302-305(1988).

Fritzsch, et al., "SH U 508, A Transpulmonary Echocontrast Agent" *Invest. Radiol.* 25(Suppl 1):160-161 (1990).

Ganguly, et al., "Structure of hollow polystyrene microspheres: an SEM study" *J. Microencapsulation* 6(2):193-198 (1989).

Gardner, "A Survey of Intraocular Gas Use in North America" *Arch. Ophthalmol.* 106(9):1188-1189 (1988).

Gottlieb, et al., "Findings of automatic border detection in subjects with left ventricular diastolic dysfunction by Doppler echocardiography" *J. Am. Soc. Echo.*, 8(2):149-161 (1995).

Handa, T., et al., "Phospholipid monolayers at the triolein-saline interface: production of microemulsion particles and conversion of monolayers to bilayers" *Biochemistry* 29:2884-2890 (1990).

*Handbook of Pharmaceutical Excipients*, U.S.A., pp. 181-183 (1986).

Hanes, *Polymer Micorspheres for Vaccine Delivery*, pp. 1-246, Massachusetts Institute of Technology: Cambridge, 1997.

Ikada et al., "Hollow microcapsular contrast media for ultrasonography and the preparation" *Chem. Abstracts*, 125(10), abs. No. 123787 (Sep. 2, 1996).

Illum & Davis, "The Organ Uptake of Intravenously administered Colloidal Particles Can Be Altered Using A Non-Ionic Surfactant (Poloxamer 338)" *FEBS Lett.* 167:79-82(1984).

Jacobs, "Intraocular gas measurement using A-scan ultrasound," *Current eye research* 5(8): 575-578 (1986).

Jacobs et al., "Behavior of intraocular gases" *Eye* 2:660-663 (1988).

Japanese Albunex Brochure.

Jongsma, "Liquids with a very low ultrasound propagation velocity" *Ultrasonics* 17(5):233 (1979).

Kabalnov, A. S., et al., "Solubility of fluorocarbons in water as a key parameter determining fluorocarbon emulsion stability" *Journal of Fluorine Chemistry* 50:271-284 (1990).

Keller, M. W., et al., "Successful Left Ventricular Opacification Following Peripheral Venou Injection of Sonicated Contrast Agent: An Experimental Evaluation" *American Heart Journal* 114(3):570-575, Sep. 1987.

Keller, et al., "The behavior of sonicated albumin microbubbles within the microcirculation: A basis for their use during myocardial contrast echocardiography" *Circulation Research* 65(2):458-467 (1989).

Klibanov, et al., "Activity of amphipathic poly(ethylene glycol) 5000 to prolong the circulation time of liposomes depends on the liposomes size and is unfavorable for immunoliposome binding to target" *Biochimica et Biophysica Acta* 1062:142-148 (1991).

Kondo, et al., eds. *Microcapsule Prcessing and Technology*, pp. 18-20, 59-92 and 106-119., Marcel Dekker, Inc.: New York (1979).

Krause, et al., "Polylactic acid nanoparticles, a colloidal drug delivery system for lipophilic drugs" *Int. J. Pharm.* 27: 145-155 (1985).

Lasic, et al., "Sterically Liposomes*: A Hypothesis On The Molecular Origin Of The Extended Circulation Times" *Biochimica et Biophysics Acta* 1070:187-192(1991).

Lee et al., "The Ocular Effects of Gases When Injected Into the Anterior Chamber of Rabbit Eyes", *Arch. Ophthalmol.* 109, 571-576 (Apr. 1991).

Lincoff, et al., "Intravitreal longevity of three perfluorocarbon gases," *Arch. Ophthalmology*, 98: 1610-1611 (1980).

Lincoff, et al., "Intravitreal expansion of perfluorocarbon bubbles," *Arch. Opthalmology*, 98: 1646 (1980).

Lincoff, et al., "The perfluorocarbon gases in the treatment of retinal detachment," *Opthalmology* 90(5): 546-551 (1983).

Lincoff et al., "Perfluoro-n-butane A gas for maximum duration retinal tamponade" *Arch. Ophthalmol.* 101(3):460-2 (1983).

Lincoff, et al., "Intravitreal disappearance rates of four perofluorocarbon gases" *Arch. Ophthalmol.* 102(6):928-9 (1984).

Long, D., et al., "Experiments With Radiopaque Perfluorocarbon Emulsions for Selective Opacification of Organs and Total Body Angiography" *Investigative Radiology* 15:242-247 (1980).

Makino, et al., "Preparation and in vitro degradation properties of polylactide microcapsules" *Chem. Pharm. Bull.* 33:1195-1201 (1985).

Marshall, Nissim, Encyclodedie Des Gaz, Encyclopedia of Gas (1976).

Maruyama, et al., "Effect of Molecular Weight In Amphipathic Polyethyleneglycol On Prolonging The Circulation Time Of Large Unilamellar Liposomes" *Chem. Pharm. Bull.* 39(6):1620-1622(1991).

Mathiowitz, "Photochemical rupture of microcapsules: A model system" *J. App. Polymer Sci.* 26:809-822 (1981).

Mathiowitz, et al., "Novel Microcapsules For Delivery Systems" *Reactive Polymers* 6:275-283(1987).

Mathiowitz, et al., "Morphology of polyanhydride microsphere delivery systems" *J Scanning Microscopy* 4(2):329-340 (1990).

Mattrey, et al., "Liver and spleen specific ultrasound contrast material" *Investigative Radiology* 17(4):Abstract 110 (1982).

Mattrey, R., et al., "Perfuorctylbromide: a liver/spleen-specific and tumor-imaging ultrsound contrast material" *Radiology* 145:759-762 (1982).

Mattrey, R., et al., "Gas Emulsions As Ultrasound Contrast Agents: Preliminary Results in Rabbits and Dogs" *Investigativ e Radiology* 29(Supplement 2):S139-141 (1994).

Mattrey, "Perfluorocarbon compounds: applications in diagnostic imaging" *SPIE* 626:18-23 (1986).

McLure et al., "Surface tension of perfluoropropane, perfluoro-n-butane, perfluoro-n-hexane, perfluoro-octane, perfluorotributylamine and n-pentane" *J. Chem. Soc. Faraday Trans.* 78:2251-2257 (1982).

Merck Index (11th Edition) Entry 2925: dextran (1989).

Meltzer, R., et al., "Why do Lungs Clear Ultrasonic Contrast?" *Ultrasound in Medicine and Biology* 6:263-269 (1980).

Meltzer, R., et al., "Transmission of Ultrasonic Contrast Through the Lungs" *Ultrasound in Medicine and Biology*, 7(4):377-384 (1981).

Miller et al, "Physiochemical approaches to the mode of action of general anesthetics" *Anesthesiology*, 36(4):339-51 (1972).

Nomura, et al., "US Contrast Enhancement of hepatic tumor with helium gas microbubbles: a preliminary report," *Jpn J. Med Ultrasonics* 18(5): 444-450 (1991) with English translation.

Ogushi, et al., "Dextran-magnetite: a new relaxation reagent and its application to $T_2$ measurements in gel systems" *Journal of Magnetic Resonance* 29: 599-601 (1978).

Ohta, T., et al., "Effect of the contrast agent and the agitation method on the size, number and stability of microbubbles: a basic experiment for the myocardial contrast study" *Japanese Journal of Medical Ultrasonics* 18:318-325 (1991), abstract.

Ophir & Parker, "Contrast Agents in Diagnostic Ultrsound" *Ultrasound in Medicine and Biology* 15(4):319-333 (1989).

Park, et al., "Solubility of gases in liquids. 14. Bunsen coefficients for several fluorine-containing gases (Freons) dissolved in water at 298. 15 K" *J. Chem. Eng. Data* 27(3):324-326 (1982).

Parker, et al., "Attenuation of Ultrasound Magnitude and Frequency Dependence for Tissue Characterization", *Radiology*, 153(3):785-788(1984).

Parker, et al., "A Particulate Contrast Agent with Potential for Ultrasound Imaging of Liver", *Ultrasound in Medicine & Biology*, 13(9):555-561(1987).

Parker & Wagg, "Measurement of Ultrasonic Attenuation Within Regions selected from B-Scan Images", *IEEE Trans. Biomed. Engr.* 30(8):431-437(1983).

Peters et al., "The Nonexpansile, Equilibrated Concentration of Perfluoropropane Gas in the Eye" *Amer. J. Ophthal.* 100:831-839 (1985).

"Polyoxyethylene Sorbitan Fatty Acid Esters" *Handbook of Pharmaceutical Excipients*, U.S.A., pp. 225-227 (1986).

Priewe, et al., "The manufacture, characterization and echogenicity testing of various micro-particles" Test Report (1999).

Raziel, "Progres recents dans la microencapsulation" *Labo-Pharma-Problemes et Techniques No.* 282: 977-982 (1978), abstract.

*Remington's Pharmaceutical Sciences*, Mack Publishing Company, pp. 295-298, 736, 1242-1244, Easton, Pennsylvania (1975).

Rovai, et al., "Contrast Echo Washout Curves From The Left Ventricle: Application Of Basic Principles Of Indicator-Dilution Theory And Calculation Of Ejection Fraction", *J. Am. Coll. Cardiol.*, 10:125-134(1987).

Sato et al., "Porous biodegradable microspheres for controlled drug delivery. I. Assessment of processing conditions and solvent removal techniques" *Pharm. Res.* 5(1):21-30 (1988).

Schlief, R., "Ultrasound contrast agents" *Current Opinion in Radiology* 3:198-207 (1991).

Schneider, et al., "Polymeric Microballoons As Ultrasound Contrast Agents Physical And Ultrasonic Properties Compared With Sonicated Albumin", *Invest. Radiol.*, 27:134-139 (1992).

Schubert, K., et al., "Microemulsifying Flourinated Oils With Mixtures of Fluorinated and Hydrogenated Surfactants" *Colloids and Surfaces: Physicochemical and Engineering Aspects* 84:97-106 (1994).

Sehgal, et al., "Influence of Postprocessing Curves on Contrast-Echographic Imaging: Preliminary Studies", *J. Ultrasound Med.*, 14:735-740(1995).

Sela, "Antigenicity: Some molecular aspects" *Science* 166: 1365-1371 (1969).

Serratrice, G., et al., "Co-colubilisation de fluorocarbures et d'eau en presence de nouveaux tensioactifs non ioniques fluores" *Journal Chim. Phys.* 87:1969-1980 (1990).

Shah, et al., "An evaluation of albumin microcapsules prepared using a multiple emulsion technique" *J. Microencapsulation* 4:223-238 (1987).

Shapiro, et al., "Intravenous Contrast Echocardiography With Use Of Sonicated Albumin In Humans: Systolic Disappearance Of Left Ventricular Contrast After Transpulmonary Transmission", *J. Am. Coll. Cardiol.*, 16:1603-1607(1990).

Smith, et al., "Left Heart Opacification With Peripheral Venous Injection Of A New Saccharide Echo Contrast Agent In Dogs", *J. Am. Coll. Cardiol.*, 13:1622-1628 (1989).

Spenlehauer, et al., "Formation and characterization of cisplatin loaded poly(d,l-lactide) microspheres for chemoemobilization" *J. Pharm. Sci.* 75: 750-755 (1986).

Swanson, "Chapter 22: Enhancement agents for ultrasound: fundamentals" in *Pharmaceuticals in Medical Imaging*, (Swanson, et al., eds.) MacMillan Publishing Company pp. 682-687, New York (1990).

Swarbrick, ed. "Polymerization procedures for biodegradable micro- and nanocapsules and particles" in *Microencapsulation and Related Drug Processess*, pp. 219-240., School of Pharmacy, University of North Carolina, Chapel Hill, N.C., 1984.

Szonyi, F., et al., "Syntheses de tensioactifs f-alkyles non ioniques monodisperses" *Journal of Fluorine Chemistry* 36:195-209 (1987), abstract.

Tice, "Biodegradable controlled release parenteral systems" *Pharm. Tech.* 26-35 (1984).

Tice, "Preparation of injectable controlled release microcapsules by a solvent evaporation process" *J. Controlled Release* 2:343-362 (1985).

Tomlinson, "Microsphere delivery systems for drug targeting and controlled release" *Int. J. Pharm. Tech. & Prod. Mfr.* 4(3):49-57 (1983).

Torchilin & Klibanov, "The Antibody-Linked Chelating Polymers for Nuclear Therapy and Diagnostics," *Critical Reviews in Therapeutic Drug Carrier Systems*, 7(4):275-307 (1991).

Tween, Sigma-Aldrich, pp. 1767.

Varescon, C., et al., "An easy, convenient was of describing the stability of fluorocarbon emulsions" *Journal de Chimie Physique* 86:2111-2116 (1989).

Vermeersch, "Immunogenicity of poly-d-lysine, a potential polymeric drug carrier" *J. Controlled Release* 32: 225-229 (1994).

Violante, M. R., et al., "Particle stabilized bubbles for enhanced organ ultrasound imaging" *Investigate Radiology* 26:194-200 (1991).

Vullo, "MRI studies of intravitreal placed gases" *Magn. Reson. Imaging* 8(Supp 1):136 (1990).

Vygantas, et al., "Octafluorocyclobutane and other gases for vitreous replacement," *Arch. OpthalmologyI*, 90: 235-236 (1973).

Walstra Encyclopedia of Emulsion Technology Becher (Dekker, 1983) 57-58 and 121.

Wen and Muccitelli, "Thermodynamics of some perfluorocarbon gases in water" *Journal of Solution Chemistry* 8(3):225-246 (1979).

Wheatley, et al., "Contrast agents for diagnostic ultrasound: development and evaluation of polymer-coated microbubbles" *Biomaterials* 11:713-717 (1990).

Widder, D. et al., "Microbubbles as a contrast agent for neurosonography and ultrasound-guided catheter manipulation: in vitro studies" *AJR* 147:347-352 (1986).

Wible, J.H., et al., "Inhaled gases affect the ultrasound contrast produced by Albunex in anesthetized dogs" *J. Am. Soc. Echocardiogr.* 9:442-451 (1996).

Wong et al., "Prediction of the kinetics of disappearance of sulfur hexafluoride and perfluoropropane intraocular gas bubbles" *Ophthalmology* 95(5):609-13 (1988).

Woodle, et al., "Versatility in Lipid Compositions Showing Prolonged Circulation With Sterically Stabilized Liposomes", *Biochimica et Biophysics Acta*, 1105:193-200(1992).

Yaws, *Matheson Gas Data Book, Seventh Edition*, pp. 146, 419, 689 and 715-721, McGraw-Hill: New York, 2001.

Zarif, L., et al., "Synergistic stabilization of perfluorocarbon-pluronic f-68 emulsion by perfluoroalkylated polyhydroxylated surfactants" *Jaocks* 66:10 (1989).

Zhu, et al., "Preparation, Characterization and Properties of Polylactide (PLA)-Poly(ethylene glyco) (PEG) Copolymers: A Potential Drug Carrier", *J. Polym. Sci., Polm. Lett. Ed.*, 24:331 (1986).

Ziskin, M., et al., "Contrast agents for diagnostic ultrasound" *Investigative Radiology* 6:500-505 (1972).

\* cited by examiner

ULTRASOUND CONTRAST AGENT DOSAGE FORMULATION

CROSS-REFERENCE TO RELATED APPLICATIONS

This application claims priority to U.S. Ser. No. 60/577,126, entitled "Ultrasound Contrast Agent Dosage Formulations" by Richard Walovitch, Howard Bernstein, Donald Chickering, and Julie Straub filed Jun. 4, 2004.

BACKGROUND OF THE INVENTION

The present invention is in the general field of diagnostic imaging agents, and is particularly directed to specific ultrasound contrast agent dosage formulations that provide enhanced images and images of long duration.

When using ultrasound to obtain an image of the internal organs and structures of a human or animal, ultrasound waves, waves of sound energy at a frequency above that discernable by the human ear, are reflected as they pass through the body. Different types of body tissue reflect the ultrasound waves differently and the reflections that are produced by the ultrasound waves reflecting off different internal structures are detected and converted electronically into a visual display.

For some medical conditions, obtaining a useful image of the organ or structure of interest is especially difficult because the details of the structure are not adequately discernible from the surrounding tissue in an ultrasound image produced by the reflection of ultrasound waves absent a contrast-enhancing agent. Detection and observation of certain physiological and pathological conditions may be substantially improved by enhancing the contrast in an ultrasound image by administering an ultrasound contrast agent to an organ or other structure of interest. In other cases, detection of the movement of the ultrasound contrast agent itself is particularly important. For example, a distinct blood flow pattern that is known to result from particular cardiovascular abnormalities may only be discernible by administering the ultrasound contrast agent to the bloodstream and observing either blood flow or blood volume.

Materials that are useful as ultrasound contrast agents operate by having an effect on ultrasound waves as they pass through the body and are reflected to create the image from which a medical diagnosis is made. Different types of substances affect ultrasound waves in different ways and to varying degrees. Moreover, certain of the effects caused by contrast-enhancing agents are more readily measured and observed than others. In selecting an ideal composition for an ultrasound contrast agent, one would prefer the substance that has the most dramatic effect on the ultrasound wave as it passes through the body. Also, the effect on the ultrasound wave should be easily measured. Gases are the preferred media for use as ultrasound contrast agents. The gas must be stabilized prior to usage as either surfactant stabilized bubbles or by encapsulating in liposomes or microparticles. There are three main contrast-enhancing effects which can be seen in an ultrasound image: backscatter, beam attenuation, and speed of sound differential.

A variety of natural and synthetic polymers have been used to encapsulate ultrasound contrast agents, such as air, in an effort to make an ultrasound contrast agent that lasts longer following administration. Schneider et al., *Invest. Radiol.*, Vol. 27, pp. 134-139 (1992) describes three micron, air-filled, synthetic, polymer particles. These particles were reported to be stable in plasma and under applied pressure. However, at 2.5 MHz, their echogenicity was low. Another type of microbubble suspension has been obtained from sonicated albumin. Feinstein et al., *J. Am. Coll. Cardiol.*, Vol. 11, pp. 59-65 (1988). Feinstein describes the preparation of microbubbles that are appropriately sized for transpulmonary passage with excellent stability in vitro. However, these microbubbles are short-lived in vivo, having a half-life on the order of a few seconds (which is approximately equal to one circulation pass) because of their instability under pressure. Gottlieb, S. et al., *J. Am. Soc. Echo.*, Vol. 3, pp. 328 (1990), Abstract; and Shapiro, J. R. et al., *J. Am. Coll. Cardiol.*, Vol. 16, pp. 1603-1607 (1990).

Gelatin-encapsulated microbubbles have also been described in WO 80/02365 by Rasor Associates, Inc. These are formed by "coalescing" the gelatin. Gas microbubbles encapsulated within a shell of a fluorine-containing material are described in WO 96/04018 by Molecular Biosystems, Inc.

Microbubbles stabilized by microcrystals of galactose (SHU 454 and SHU 508) have also been reported by Fritzch et al. Fritzsch, T. et al., *Invest. Radiol.* Vol. 23 (Suppl 1), pp. 302-305 (1988); and Fritzsch, T. et al., *Invest. Radiol.*, Vol. 25 (Suppl 1), 160-161 (1990). The microbubbles last up to 15 minutes in vitro but less than 20 seconds in vivo. Rovai, D. et al., *J. Am. Coll. Cardiol.*, Vol. 10, pp. 125-134 (1987); and Smith, M. et al., *J. Am. Coll. Cardiol.*, Vol. 13, pp. 1622-1628 (1989). EP 398 935 by Schering Aktiengesellschaft discloses the preparation and use of microencapsulated gas or volatile liquids for ultrasound imaging, where the microcapsules are formed of synthetic polymers or polysaccharides. European Patent 458 745 by Sintetica discloses air or gas microballoons bounded by an interfacially deposited polymer membrane that can be dispersed in an aqueous carrier for injection into a host animal or for oral, rectal, or urethral administration, for therapeutic or diagnostic purposes.

WO 92/18164 by Delta Biotechnology Limited describes the preparation of microparticles by spray drying an aqueous protein solution to form hollow spheres having gas entrapped therein, for use in imaging. WO 93/25242 describes the synthesis of microparticles for ultrasonic imaging consisting of a gas contained within a shell of polycyanoacrylate or polyester. WO 92/21382 discloses the fabrication of microparticle contrast agents which include a covalently bonded matrix containing a gas, wherein the matrix is a carbohydrate. U.S. Pat. Nos. 5,334,381, 5,123,414 and 5,352,435 to Unger describe liposomes for use as ultrasound contrast agents, which include gases, gas precursors, such as a pH activated or photo-activated gaseous precursor, as well as other liquid or solid contrast enhancing agents.

Others have looked at the effect of the gas which is encapsulated, and suggested the use of fluorinated gases to enhance imaging as compared to air. U.S. Pat. No. 5,393,524 to Quay discloses the use of agents, including perfluorocarbons, for enhancing the contrast in an ultrasound image. The agents consist of small bubbles, or microbubbles, of selected gases, which exhibit long life spans in solution and are small enough to traverse the lungs, enabling their use in ultrasound imaging of the cardiovascular system and other vital organs. EP 554213 by Bracco discloses the use of fluorinated hydrocarbon gases to prevent collapse of microvesicles upon exposure to pressure in the bloodstream. WO 95/23615 by Nycomed discloses microcapsules for imaging which are formed by coacervation of a solution, for example, a protein solution, containing a perfluorocarbon. WO 95/03357 by Massachusetts Institute of Technology discloses microparticles formed of polyethylene glycol-poly(lactide-co-glycolide) block polymers having imaging agents encapsulated therein, including gases such as air and perfluorocarbons. As described in WO 94/16739 by Sonus Pharmaceuticals, Inc., while solids and liquids reflect sound to a similar degree, gases are known to be more efficient and are the preferred media for use as ultrasound contrast agents. In fact, as shown by Example 12 of WO 94/16739, protein microcapsules were dismissed as raising safety concerns (as well as efficacy issues) when administered to mini-pigs. U.S. Pat. Nos. 6,132, 699 and 5,611,344 both describe methods of enhancing contrast using perfluorocarbon gases in synthetic polymeric shells. U.S. Pat. No. 5,837,221 describes a method of making a porous polymeric microparticle having a hydrophobic agent incorporated into the polymer to increase echogenicity.

Several ultrasound contrast agents have been approved in either the United States or Europe for very limited cardiac applications. OPTISON® (Amersham, Mallinkrodt) consists of heat denatured human albumin microcapsules containing the gas octafluoropropane. Each mL of microsphere suspension contains $5-8\times10^8$ microspheres with a mean diameter in the 2-4.5 micron size range and 220 µg octafluoropropane. These microspheres have not been approved for myocardial blood flow assessment and have only been approved for ventricular chamber enhancement. At high bolus doses (5 mL suspension or 1100 µg octafluoropropane), ventricular chamber enhancement lasts up to 5 minutes.

DEFINITY® (Bristol Myers Medical Imaging) consists of octafluoropropane containing lipid microspheres where the lipid shell is comprised of the phospholipids DPPA, DPPC, and mPEG-DPPE. Each mL of suspension contains $1.2\times10^{10}$ microparticles having a mean diameter in the 1.1-3.3 micron size range and 1100 µg of octafluoropropane. The agent is only approved for ventricular chamber enhancement and not myocardial blood flow assessment. At a bolus dose of 700 µL (for a 70 kg person) or 5133 µg of gas, the agent has an enhancement duration in the ventricular chambers of approximately 3.4 minutes.

IMAGENT® (Photogen Inc.) consists of lipid microspheres containing pefluorohexane where the lipid shell is comprised of the phospholipid DMPC. Each mL of suspension contains $1.4\times10^9$ microparticles having a mean diameter less than 3 microns and 92 µg of perfluorohexane. The agent is only approved for ventricular chamber enhancement and not myocardial blood flow assessment. At a bolus dose of 0.43 mL (for a 70 kg person) or 40 µg of gas, the agent has a mean enhancement duration in the ventricular chambers of approximately 2.6 minutes.

In all cases, these commercial agents have limited utility and are not approved for applications other than ventricular chamber enhancement and provide mean image enhancement durations in the ventricular chambers lasting for periods of 5 minutes or less. There is a lack of commercial ultrasound contrast agents which allow enhanced images of the cardiovascular system, particularly of the myocardium and the ventricular chambers, for long duration. The agents described in the prior art when administered as a bolus or short infusion result in images of the myocardium which last for significantly less time than the amount of time required to conduct a complete examination of the heart. Typically, the prior art agents provide images that last for well below one minute for the myocardium. An agent that can provide enhanced image durations exceeding one minute in the myocardium and/or greater than 5 minutes in the ventricular chambers is desirable.

It is therefore an object of the invention to provide a dosage formulation containing microparticles that provides enhanced images and images of long duration, particularly for cardiac applications.

It is another object of the invention to provide a kit for administering the dosage formulation containing microparticles for use in ultrasound imaging techniques.

SUMMARY OF THE INVENTION

Clinical studies have been conducted and specific dosage formulations developed using polymeric microparticles having incorporated therein perfluorocarbon gases that provide significantly enhanced images of long duration. The dosage formulation typically includes one, two or up to five doses, most preferably one or two doses, of microparticles formed of a biocompatible polymer, preferably including a lipid incorporated therein, and containing a perfluorocarbon that is a gas at body temperature. The microparticles are administered to a patient in a dose effective to enhance ultrasound imaging in the ventricular chambers for more than five minutes and/or in the mycocardium for more than a minute, and a dose ranging from 0.025 to 8.0 mg microparticles/kg body weight. Preferably the dose administered to a patient ranges from 0.05 to 4.0 mg microparticles/kg body weight. In a preferred embodiment, the ultrasound imaging is enhanced in the ventricular chambers for more than 9 minutes and/or in the myocardium for more than 2 minutes.

The dosage formulation typically is provided in a vial or in a syringe. In a typical formulation, the dosage formulation is in the form of a dry powder that is reconstituted with sterile water prior to use by adding the water to the vial or syringe of the dry powder and shaking to yield an isosmotic or isotonic suspension of microparticles. In the preferred embodiment of this dosage formulation, the suspension contains $1.0-3.5\times10^9$ microparticles/mL of suspension or 25-50 mg microparticles/ mL of suspension with the most preferred concentration yielding a suspension containing $1.5-2.8\times10^9$ microparticles/ mL of suspension or 30-45 mg microparticles/mL of suspension. In a preferred embodiment, the microparticles have a mean particle size less than 8 microns, more preferably a mean particle size of 1.8-3.0 microns, and most preferably a mean particle size of 1.9-2.6 microns.

In a preferred embodiment, the gas is $CF_4$, $C_2F_4$, $C_2F_6$, $C_3F_6$, $C_3F_8$, $C_4F_8$, $C_4F_{10}$, or $SF_6$. In preferred embodiments, the gas is n-perfluorobutane ($C_4F_{10}$) provided in an amount between 75-500 µg/mL of administered volume of microparticle suspension; preferably the n-perfluorobutane is provided in an amount between 100-400 µg/mL of administered volume of microparticle suspension and most preferably between 150-350 µg/mL of administered volume of microparticle suspension; or the gas is n-octafluoropropane provided in an amount between 75-375 µg/mL of administered volume of microparticle suspension, most preferably between 120-300 µg/mL of administered volume of microparticle suspension.

In the most preferred embodiment, the microparticle is formed of a synthetic polymer such as poly(hydroxy acids) which include poly(lactic acid), poly(glycolic acid), and poly (lactic acid-co-glycolic acid), polyglycolides, polylactides, and poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly (ethylene oxide) polyvinyl alcohols, poly(valeric acid), and poly(lactide-co-caprolactone), derivatives, copolymers and blends thereof and includes a hydrophobic compound incorporated with the polymer at a ratio of between 0.01 and 30% by weight of hydrophobic compound to weight of polymer, most preferably a lipid incorporated with the polymer at a ratio of between 0.01 and 30% (weight lipid/weight polymer). In a particularly preferred embodiment, the lipid is dioleoylphosphatidylcholine (DOPC), dimyristoylphosphatidylcholine (DMPC), dipentadecanoylphosphatidylcholine (DPDPC) dilauroylphosphatidylcholine (DLPC), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLGPC); or a phosphatidylethanolamine.

Most preferably, the synthetic polymer in the microparticles is poly(lactide-co-glycolide), with a lactide to glycolide ratio of 50:50 (i.e. 1:1) and a weight average molecular weight in the range 20,000-40,000 Daltons, and the hydrophobic compound in the microparticles is DAPC, in a ratio of 5 to 6.6% (weight DAPC/weight polymer).

The dosage formulation may be provided as a vial or a syringe of dry powder containing microparticles or in a kit including a solution for resuspending the microparticles. Typically the vial or syringe of dry powder will also include excipients such as sugars or salts to make the solution isosmotic or isotonic after reconstitution. This dosage formulation is then administered to a patient to be imaged by injection, either as a bolus or an injection over a period of up to 30 minutes.

The microparticles are useful in a variety of diagnostic imaging procedures including ultrasound imaging, magnetic resonance imaging, fluoroscopy, x-ray, and computerized tomography. The microparticles were tested in clinical trials for cardiology applications such as myocardial blood flow assessment and ventricular chamber enhancement.

DETAILED DESCRIPTION OF THE INVENTION

Improved methods, microparticles, kits, and dosage formulations for ultrasound imaging are described herein. The microparticles are useful in a variety of diagnostic ultrasound imaging applications, particularly in ultrasound procedures such as blood vessel imaging and echocardiography such as myocardial blood flow assessment, myocardial blood volume assessment and ventricular chamber enhancement.

I. Definitions

As generally used herein, the term "microparticle" includes "microspheres" and "microcapsules", as well as other microparticles, unless otherwise specified. Microparticles may or may not be spherical in shape. "Microcapsules" are defined herein as microparticles having an outer polymer shell surrounding a core of a gas. "Microspheres" as defined herein can be solid polymeric spheres, or porous spheres with a honeycombed structure or sponge like structure formed by pores throughout the polymer that are filled with a gas. Some microspheres may contain an outer polymer shell with a honeycombed structure or a sponge like structure formed by pores throughout the polymer shell and the pores are filled with gas. For this type of microsphere, this outer polymer shell surrounds an internal core of gas.

As generally used herein, the terms "dosage" and "dose" are used synonymously to refer to the amount of a substance that is given at one time or the amount of substance that is required to produce the desired diagnostic or contrast effect.

As used herein, the term "dosage formulation" refers to a vial or other container such as a syringe, containing one or more dosages of substance required to produce the desired diagnostic or contrast effect.

As generally used herein "region of a patient" refers to a particular area or portion of the patient. In some instances "region of patient" refers to regions throughout the entire patient. Examples of such regions are the pulmonary region, the gastrointestinal region, the cardiovascular region (including myocardial tissue or myocardium (i.e. heart muscle), ventricular chambers, atrial chambers, valve function), the renal region as well as other body regions, tissues, organs and the like, including the vasculature and circulatory systems, and as well as diseased tissue, including cancerous tissue. "Region of a patient" includes, for example, regions to be imaged with diagnostic imaging. The "region of a patient" is preferably internal, although it may be external.

As generally used herein "vasculature" denotes blood vessels (including arteries, veins, capillaries and the like).

As generally used herein "gastrointestinal region" includes the region defined by the esophagus, stomach, small and large intestines, and rectum.

As generally used herein "renal region" refers to the region defined by the kidney and the vasculature that leads directly to and from the kidney, and includes the abdominal aorta.

As generally used herein "region to be targeted" and "targeted region" are used interchangeably to refer to a region of a patient where delivery of an agent is desired.

As generally used herein "region to be imaged" and "imaging region" are used interchangeably to refer to a region of a patient where imaging is desired.

As generally used herein "ventricular blood flow or ventricular chamber enhancement" refers to the flow of blood through the ventricles of the heart in one or more cardiac cycles.

As generally used herein "atrial blood flow" refers to the flow of blood through the atria of the heart in one or more cardiac cycles.

As generally used herein "myocardial blood flow" refers to the flow of blood in the vasculature of the heart muscle or myocardium, including the blood vessels in the heart, in one or more cardiac cycles.

As generally used herein "myocardial blood volume" refers to the volume of blood in the vasculature of the heart muscle or myocardium.

As generally used herein "cardiac cycle" refers to a complete contractile period of the heart, and includes both the diastole and systole periods.

As generally used herein "increased brightness" refers to an increase in the brightness of an image compared to an image obtained without an ultrasound contrast agent.

As generally used herein "enhanced image" refers to an image which has increased brightness relative to an image obtained without an ultrasound contrast agent.

As generally used herein "duration" refers to the total time over which increased brightness of an image can be detected.

As generally used herein "coronary vasodilator" refers to a bioactive agent such as dipyridamole or adenosine which, when administered to a patient, causes dilation of the vasculature in the cardiovascular region.

II. Microparticles

In the preferred embodiment, the microparticles contain a polymer, a lipid and a perfluorocarbon gas. Microparticles may consist of both microspheres and microcapsules, or only microspheres or microcapsules.

Polymers

In the preferred embodiment, the microparticles are formed from synthetic polymers. Synthetic polymers produce microparticles that are biocompatible and are not contaminated by biological materials. Additionally, synthetic polymers are preferred due to more reproducible synthesis and degradation both in vitro and in vivo. The polymer is selected based on the time required for in vivo stability, i.e., that time required for distribution to the site where imaging is desired, and the time required for imaging. Synthetic polymers may be modified to produce microparticles with different properties (e.g. changing molecular weight and/or functional groups).

Representative synthetic polymers are: poly(hydroxy acids) such as poly(lactic acid), poly(glycolic acid), and poly(lactic acid-co-glycolic acid), polyglycolides, polylactides, poly(lactide-co-glycolide) copolymers and blends, polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide) polyvinyl alcohols, poly(valeric acid), and poly(lactide-co-caprolactone), derivatives, copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, polylactide, polyglycolide, poly(lactide-co-glycolide), and copolymers with PEG, polyanhydrides, poly(ortho)esters, polyurethanes, poly(butyric acid), poly(valeric acid), poly(lactide-co-caprolactone), blends and copolymers thereof. The most preferred polymer is poly(lactide-co-glycolide) with a lactide to glycolide ratio of 50:50 (i.e. 1:1) and the polymer having a weight average molecular weight in the range 20,000-40,000 Daltons. The weight average molecular weight ($M_w$) of the polymer is the average molecular weight calculated on the basis of the mass of molecules with a given molecular weight within the distribution of individual polymer chains. $M_w$ can be determined using gel permeation chromatography (GPC).

Hydrophobic Compounds

In the preferred embodiment, the polymer includes a hydrophobic compound, as described in U.S. Pat. No. 5,837,221. In general, incorporation of compounds such as lipids which are hydrophobic and in an effective amount within the polymers, limits penetration and/or uptake of water by the microparticles and thus limits gas loss from the microparticles. This is effective in increasing the duration of enhanced imaging provided by microparticles that contain a lipid, a synthetic polymer and a gas encapsulated therein, especially fluorinated gases such as perfluorocarbons. Lipids which may be used to stabilize gas inside the polymeric microparticles include but are not limited to the following classes of lipids: fatty acids and derivatives, mono-, di and triglycerides, phospholipids, sphingolipids, cholesterol and steroid derivatives, terpenes and vitamins.

Fatty acids and derivatives thereof may include but are not limited to saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that may be used include, but are not limited to, molecules that have between 12 carbon atoms and 22 carbon atoms in either linear or branched form. Examples of saturated fatty acids that may be used include, but are not limited to, lauric, myristic, palmitic, and stearic acids. Examples of unsaturated fatty acids that may be used include, but are not limited to lauric, physeteric, myristoleic, palmitoleic, petroselinic, and oleic acids. Examples of branched fatty acids that may be used include, but are not limited to, isolauric, isomyristic, isopalmitic, and isostearic acids and isoprenoids. Fatty acid derivatives include 12-(((7'-diethylaminocoumarin-3 yl)carbonyl)methylamino)-octadecanoic acid; N-[12-(((7'diethylaminocoumarin-3-yl)carbonyl)methylamino)octadecanoyl]-2-aminopalmitic acid, N succinyl-dioleoylphosphatidylethanol amine and palmitoyl-homocysteine; and/or combinations thereof. Mono, di and triglycerides or derivatives thereof that may be used include, but are not limited to molecules that have fatty acids or mixtures of fatty acids between 6 and 24 carbon atoms, digalactosyldiglyceride, 1,2-dioleoyl-sn-glycerol; 1,2-dipalmitoyl-sn-3 succinylglycerol; and 1,3-dipalmitoyl-2-succinylglycerol.

Phospholipids which may be used include but are not limited to phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-alkyl phospholipids. Examples of phospholipids include, but are not limited to, phosphatidylcholines such as dioleoylphosphatidylcholine (DOPC), dimyristoylphosphatidylcholine (DMPC), dipentadecanoylphosphatidylcholine (DPDPC), dilauroylphosphatidylcholine (DLPC), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

Sphingolipids which may be used include ceramides, sphingomyelins, cerebrosides, gangliosides, sulfatides and lysosulfatides. Examples of sphinglolipids include, but are not limited to, the gangliosides GM1 and GM2.

Steroids which may be used include but are not limited to cholesterol, cholesterol sulfate, cholesterol hemisuccinate, 6-(5-cholesterol 3β-yloxy)hexyl-6-amino-6-deoxy-1-thio-α-D-galactopyranoside, 6-(5-cholesten-3β-tloxy)hexyl-6-amino-6-deoxyl-1-thio-α-D mannopyranoside and cholesteryl) 4'-trimethyl 35 ammonio)butanoate.

Additional lipid compounds which may be used include tocopherol and derivatives, and oils and derivatized oils such as stearlyamine.

A variety of cationic lipids such as DOTMA, N-[1-(2,3-dioleoyloxy) propyl-N,N,N-trimethylammonium chloride; DOTAP, 1,2-dioleoyloxy-3-(trimethylammonio)propane; and DOTB, 1,2-dioleoyl-3-(4'-trimethyl-ammonio)butanoyl-sn-glycerol may be used.

The most preferred lipids are phospholipids, preferably DPPC, DAPC, DSPC, DTPC, DBPC, DLPC and most preferably DPPC, DSPC, DAPC and DBPC.

The lipid content ranges from 0.01-30% (w lipid/w polymer); preferably between 0.1-20% (w lipid/w polymer) and most preferably 1-12% (w lipid/w polymer).

When formed by the methods described herein, the size of the microparticles is consistently reproducible. As used herein, the terms "size" or "diameter" in reference to particles refers to the number average particle size, unless otherwise specified. An example of an equation that can be used to define the number average particle size ($X_n$) is shown below:

$$X_n = \frac{\sum_{i=1}^{\infty} n_i d_i}{\sum_{i=1}^{\infty} n_i}$$

where $n_i$=number of particles of a given diameter ($d_i$).

As used herein, the term "volume average diameter" refers to the volume weighted diameter average. An example of equations that can be used to define the volume average diameter ($X_v$) is shown below:

$$X_v = \left[\frac{\sum_{i=1}^{\infty} n_i d_i^3}{\sum_{i=1}^{\infty} n_i}\right]^{1/3}$$

where $n_i$=number of particles of a given diameter ($d_i$).

Particle size analysis can be performed on a Coulter counter, by light microscopy, scanning electron microscopy, transmittance electron microscopy, laser diffraction methods such as those using a Malvern Mastersizer, light scattering methods or time of flight methods. As used herein "Coulter method" refers to a method in which the powder is dispersed in an electrolyte, and the resulting suspension analyzed using a Coulter Multisizer II fitted with a 50-μm aperture tube. This method provides size measurements and particle concentrations.

In the preferred embodiment for the preparation of injectable microparticles capable of passing through the pulmonary capillary bed, the microparticles have a diameter less than eight microns. Larger microparticles may clog the pulmonary bed, and smaller microparticles may not provide sufficient contrast effect. The preferred microparticle size for an intravenously administered ultrasound contrast agent is between 0.75 microns and 5 microns, more preferably between 1.8 and 3.0 microns, and most preferably between 1.9 and 2.6 microns.

In the preferred embodiment, the microparticles have a honeycombed structure or sponge like structure, formed by pores throughout the polymer or the microparticles have a polymeric shell with a honeycombed or sponge like, porous structure. In both cases the pores are filled with gas. These microparticles are formed by spray drying a polymer solution containing a pore forming agent such as a volatile salt as described below.

Ultrasound Contrast Imaging Agents

Examples of fluorinated gases include $CF_4$, $C_2F_4$, $C_2F_6$, $C_3F_6$, $C_3F_8$, $C_4F_8$, $C_4F_{10}$, and $SF_6$. Preferably the gas is a perfluorocarbon that is a gas at body temperature, such as $CF_4$, $C_2F_4$, $C_2F_6$, $C_3F_6$, $C_3F_8$, $C_4F_8$, and $C_4F_{10}$. n-Perfluorobutane ($C_4F_{10}$) is particularly preferred because it provides an insoluble gas that will not condense at the temperature of use and is pharmacologically acceptable.

The amount of gas contained with the microparticles will depend on the type of gas but is typically between 75-500 μg/mL of administered volume of microparticle suspension. For n-perfluorobutane, the preferred gas content is between 100-400 μg/mL of administered volume of microparticle suspension and most preferably is between 150-350 μg/mL of administered volume of microparticle suspension. For n-octafluoropropane, the preferred gas content is between 75-375 μg/mL of administered volume of microparticle suspension, and most preferably between 120-300 μg/mL of administered volume of microparticle suspension.

III. Methods for making Microparticles

The microparticles may be produced by a variety of methods, and are preferably produced by spray drying. A major criterion is that the polymer must be dissolved or melted with the hydrophobic compound or lipid, prior to forming the microparticle.

Solvents

During formation, the polymer is generally dissolved in a solvent. As defined herein, the polymer solvent is an organic solvent that is volatile or has a relatively low boiling point or can be removed under vacuum and which is acceptable for administration to humans in trace amounts, such as methylene chloride. Other solvents, such as ethyl acetate, ethyl formate, ethanol, methanol, dimethyl formamide (DMF), acetone, acetonitrile, tetrahydrofuran (THF), formamide, acetic acid, dimethyl sulfoxide (DMSO) and chloroform also may be utilized, or combinations thereof. In general, the polymer is dissolved in the solvent to form a polymer solution having a concentration of between 0.1 and 60% weight to volume (w/v), more preferably between 0.25 and 30% (w/v) and most preferably between 0.5-10% (w/v).

Spray Drying

Microparticles are preferably produced by spray drying by dissolving a biocompatible polymer and lipid in an appropriate solvent, dispersing a pore forming agent as a solid or as a solution into the polymer solution, and then spray drying the polymer solution and the pore forming agent, to form microparticles. As defined herein, the process of "spray drying" a solution of a polymer and a pore forming agent refers to a process wherein the polymer solution and pore forming agent are atomized to form a fine mist and dried by direct contact with hot carrier gases. Using spray dryers available in the art, the polymer solution and pore forming agent may be atomized at the inlet port of the spray dryer, passed through at least one drying chamber, and then collected as a powder. The temperature may be varied depending on the gas or polymer used. The temperature of the inlet and outlet ports can be controlled to produce the desired products.

The size and morphology of the microparticles formed during spray drying is a function of the nozzle used to spray the polymer solution and the pore forming agent, the nozzle pressure, the flow rate of the polymer solution with the pore forming agent, the polymer used, the concentration of the polymer in solution, the type of polymer solvent, the type and the amount of pore forming agent, the temperature of spraying (both inlet and outlet temperature) and the polymer molecular weight. Generally, the higher the polymer molecular weight, the larger the particle size, assuming the polymer solution concentration is the same.

Typical process parameters for spray drying are as follows: inlet temperature=30-200° C., outlet temperature=5-100° C., and polymer flow rate=10-5,000 ml/min.

A gaseous diagnostic agent may be encapsulated by emulsifying the gas with the polymer solution and the pore forming agent prior to spray drying. Alternatively, air filled microparticles can be produced during the spray drying step and subsequently the air replaced with the perfluorocarbon gas by applying a stream of the desired gas to the microparticles, or pulling a vacuum on the microparticles to remove the encapsulated air, then filling with the desired perfluorocarbon gas. A lyophilizer or vacuum chamber may be used if a vacuum step is used to exchange the gas.

Additives to Facilitate Microparticulate Formation

A variety of surfactants may be added during the formation of the microparticles. Exemplary emulsifiers or surfactants which may be used (0.1-15% w/w polymer) include most physiologically acceptable emulsifiers. Examples include natural and synthetic forms of bile salts or bile acids, both conjugated with amino acids and unconjugated such as taurodeoxycholate, and cholic acid.

Pore forming agents are included in the polymer solution in an amount of between 0.01% and 90% weight to volume of polymer solution, to increase pore formation. For example, in spray drying, a pore forming agent such as a volatile salt, for example, ammonium bicarbonate, ammonium acetate, ammonium carbonate, ammonium chloride or ammonium benzoate or other volatile salt as either a solid or as a solution in a solvent such as water can be used. The solid pore forming agent or the solution containing the pore forming agent is then emulsified with the polymer solution to create a dispersion or droplets of the pore forming agent in the polymer. This dispersion or emulsion is then spray dried to remove both the polymer solvent and the pore forming agent. After the polymer is precipitated, the hardened microparticles can be frozen and lyophilized to remove any pore forming agent not removed during the polymer precipitation step.

The preferred microparticle is formed using the polymer, poly(lactide-co-glycolide) with a lactide to glycolide ratio of 50:50 and having a weight average molecular weight in the range 20,000-40,000 Daltons, and the phospholipid, diarachidoylphosphatidylcholine ((1,2-diarachidoyl-sn-glycero-3-phosphocholine (DAPC)) at a ratio of 5-6.6% (w DAPC/w polymer). The microparticles are further formulated in a solution of mannitol and TWEEN® 80 and processed to yield a dry powder of microparticles which are backfilled on a lyophilizer with n-perfluorobutane. The dry powder is reconstituted with 5 mL of sterile water prior to use by adding the water to the vial of the dry powder and shaking to yield a suspension of microparticles in isosmotic mannitol. The preferred properties of the suspension are a gas content of 150-350 μg/mL of n-perfluorobutane per administered volume of microparticle suspension, $1.5-2.8\times10^9$ microparticles/mL of administered volume of microparticle suspension, 30-45 mg microparticles/mL of administered volume of microparticle suspension, and a mean particle size in the range 1.8-3.0 microns.

IV. Applications for the Microparticles

1. Formulations for Administration to a Patient

The microparticles may undergo further processing with excipients to create a dry powder. The excipients provide tonicity or osmolarity or ease of suspendability of the microparticles after reconstitution with a pharmaceutically acceptable carrier prior to administration to a patient. Excipients suitable for providing osmolarity or tonicity are sugars including but not limited to mannitol, dextrose or glucose and salts including but not limited to sodium chloride or sodium phosphate. Excipients suitable for providing ease of suspendability of the microspheres include any pharmaceutically acceptable wetting agent or surfactant including but not limited to polysorbate 80 (TWEEN® 80), polysorbate 20 (TWEEN® 20), Pluronic or polyethylene glycol. Excipients suitable for providing osmolarity or tonicity or that can be used as wetting agents are described in references such as the Handbook of Pharmaceutical Excipients (Fourth Edition, Royal Pharmaceutical Society of Great Britain, Science & Practice Publishers) or Remingtons: The Science and Practice of Pharmacy (Nineteenth Edition, Mack Publishing Company). The dry powder of microparticles and excipients is created by suspending the microparticles in a solution of excipients. Further size fractionation steps may be used if needed. The microparticles in the solution of excipients are filled into vials or syringes, frozen, and lyophilized to create the dry powder formulation. At the conclusion of the lyophilization step, the microparticles are filled with the perfluorocarbon gas by backfilling the lyophilizer with the perfluorocarbon gas. The vials or syringes are then stoppered or capped and in the case of vials, crimped. This results in a perfluorocarbon headspace in the vial or syringe.

Alternatively, the microparticles can be dry blended with the pharmaceutical excipients and then filled into vials or syringes. The microparticles can be filled with the perfluorocarbon gas by applying a vacuum after loading the vials or syringes on a lyophilizer or in a vacuum chamber. The vials or syringes are then stoppered or capped and in the case of vials, crimped. This results in a perfluorocarbon headspace in the vial or syringe.

2. Dosage Units

Different size dosage units of microparticles may be used. For example a small dosage unit may contain 25-75 mg of microparticles. An intermediate dosage unit may contain 75-150 mg. A large dosage unit may contain 150-250 mg of microparticles. An extra large dosage unit may contain 250-1000 mg of microparticles.

When the suspension of microparticles is formed following reconstitution, the mass concentration of microspheres in the suspension typically ranges from 20 to 60 mg/mL. The preferred mass concentration of microspheres in the suspension is 25-50 mg/mL; and the most preferred mass concentration of microspheres in the suspension is 30 to 45 mg/mL. The preferred concentration of microparticles in the suspension is $1.0-3.5\times10^9$ microparticles/mL of suspension; and the most preferred concentration of microparticles in the suspension is $1.5-2.8\times10^9$ microparticles/mL. The microparticles have a preferred mean particle size of less than 8 microns, more preferably in the range of 1.8-3.0 microns, and most preferably in the range of 1.9-2.6 microns.

Pharmaceutically acceptable carriers may include water for injection, sterile water, saline, saline containing glycerol, saline containing TWEEN® 20, saline containing TWEEN® 80, isosmotic dextrose (5%), ½ isosmotic dextrose (2.5%), isosmotic mannitol (5%), ½ isosmotic mannitol (2.5%), isotonic mannitol containing TWEEN® 20 and isotonic mannitol containing TWEEN® 80.

3. Kits

Kits for parenteral administration of the microparticles containing the perfluorocarbon gas may be provided. The kit contains at least two components. One component contains a dosage unit of the dry powder contrast agent in a vial or syringe, and the other component contains a pharmaceutically acceptable carrier in a vial or syringe. Prior to administration to a patient, the pharmaceutically acceptable carrier is added to the dosage unit of the dry powder contrast agent to form a suspension of gas filled microparticles that are usable as an ultrasound imaging contrast agent in diagnostic imaging by any route of administration.

4. Vials or Containers for microparticles

No specific vial or syringe or connection systems are required for the kits; conventional vials, syringes and adapters may be used with the microparticles. The only requirement for a vial is a good seal between the stopper and the container. The quality of the seal, therefore, becomes a matter of primary concern; any degradation of seal integrity could allow undesirables substances to enter the vial or allow the gas to escape. In addition to assuring sterility, vacuum retention is essential for products stoppered at reduced pressures to assure safe and proper reconstitution. As to the stopper, it may be a compound or multicomponent formulation based on an elastomer, such as poly (isobutylene) or "butyl rubber" and must be impermeable to the gas used. The vial size is selected depending on the total dosage of dry powder in the vial. Preferred vial sizes are 5mL, 10 mL, 20 mL and 30 mL. The syringe size is selected depending on the total dosage of dry powder in the syringe. Preferred syringe sizes are 5 mL, 10 mL, 20 mL, and 50 mL syringes.

5. Diagnostic Applications

The microparticle compositions may be used in many different diagnostic applications including ultrasound imaging, magnetic resonance imaging, fluoroscopy, x-ray, and computerized tomography.

In the preferred embodiment, the microparticles are used in ultrasound procedures such as blood vessel imaging and echocardiography including but not limited to ventricular chamber imaging, myocardial blood flow assessment, myocardial blood volume assessment, diagnosis of coronary artery disease, and ejection fraction assessment.

The microparticles may be used in vascular imaging, as well as in applications to detect liver and renal diseases, in detecting and characterizing tumor masses and tissues, and in measuring peripheral blood velocity. The microparticles also can be linked with ligands that minimize tissue adhesion or that target the microparticles to specific regions of the body in vivo.

General Method of Obtaining Images

The microparticles in dry powder form are reconstituted with a pharmaceutically acceptable carrier prior to administration, then an effective amount for detection is administered to a patient using an appropriate route, by injection into a blood vessel (such as intravenously (i.v.) or intra-arterially (i.a.)), or orally. The microparticle composition may be administered intravenously to the patient as a bolus injection or short infusion (less than 30 minutes). Preferably the injection is administered over a time period ranging from 15 seconds to 20 minutes, most preferably ranging from 30 seconds to 15 minutes. Typically, a dose ranging from 0.025 to 8 mg/kg body weight per injection is administered intravenously to a patient, preferably the dose ranges from 0.05 to 4 mg/kg.

For diagnostic ultrasound applications, energy is applied to at least a portion of the patient to image the target tissue. A visible image of an internal region of the patient is then obtained, such that the presence or absence of diseased tissue can be ascertained. Ultrasonic imaging techniques, including second harmonic imaging and gated imaging, are well know in the art and are described, for example, in Uhlendorf, *IEEE Transactions on Ultrasonics, Ferroelectrics, and Frequency Control*, 14(1):70-79 (1994) and Sutherland, et al., *Journal of the American Society of Echocardiography*, 7(5):441-458 (1994), the disclosures of each is hereby incorporated herein by reference in its entirety.

Ultrasound waves may be applied with a transducer. The ultrasound can be pulsed or it may be continuous, if desired. Thus, diagnostic ultrasound generally involves the application of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the imaging agents, which may be targeted to a desired site, for example, blood clots. Other harmonic signals, such as odd harmonics signals, for example, 3x or 5x, would be similarly received using this method. Subharmonic signals, for example, x/2 and x/3, may also be received and processed so as to form an image.

In addition, Power Doppler or Color Doppler may be applied. In the case of Power Doppler, the relatively higher energy of the Power Doppler may resonate the vesicles. This can create acoustic emissions which may be in the subharmonic or ultraharmonic range or in some cases, in the same frequency as the applied ultrasound.

Specific Imaging Applications

The microparticles described herein can be used in both cardiology and radiology applications. For cardiology applications, the microparticle compositions are administered to a patient and the patient is scanned using an ultrasound machine to obtain visible images of the cardiovascular region. Optionally the microparticle composition is administered in combination with a pharmacological stressor or a physical stressor. Suitable pharmacological stressors include a coronary vasodilator such as dipyridamole or adenosine, an inotropic agent (i.e. increases the strength of heart contraction) such as dobutamine or a chronotropic agent (i.e. increases the frequency of contraction) such as dobutamine. Suitable physical stressors include physical exercise, such as by using a treadmill or a stationary bicycle.

For radiology applications, the microparticle compositions are administered to a patient and the patient is scanned using an ultrasound machine to obtain visible images of the region of a patient to be examined.

The microparticles can be used to assess the function of the cardiovascular system as well as to assess myocardial blood flow or myocardial blood volume or to diagnose coronary heart disease (coronary artery disease). For example the microparticles can enhance images of the ventricular chambers and thus assist in regional cardiac function analysis through wall motion analysis and assist in global cardiac function through ejection fraction measurements. The microparticles can also be used to assess myocardial blood flow to differentiate functioning cardiac tissue from either ischemic (blood flow deficient) cardiac tissue or infarcted (dead) cardiac tissue. The contrast signals detected in the myocardium can be used as an estimate of myocardial blood volume since ultrasound contrasts agents reside intravascularly following intravenous administration. The absence or reduction in contrast intensity or image brightness in a particular myocardial region over time is indicative of reduced blood flow (i.e. a defect).

Most often unless the patient has severe coronary heart disease, blood flow to the various regions of the heart as assessed by techniques such as ultrasound contrast will appear normal. In order to detect blood flow abnormalities in patients without severe heart disease or to detect smaller myocardial blood flow defects, it is necessary to increase the blood flow requirements to the heart by inducing a state of stress. Stress can be induced by having the patient exercise or by administering a pharmacological compound such as a vasodilator, an inotropic agent or a chronotropic agent. During exercise or pharmacological stress, blood flow defects can be more easily detected because the ability to increase blood flow is reduced in regions supplied by coronary arteries with stenosis. A comparison of ultrasound images of the myocardium following ultrasound contrast agent administration can be made both in the pre-stress state (i.e. rest state) and in the stress state. A myocardial region without enhanced brightness found during stress imaging but not during rest imaging is indicative of ischemia. A myocardial region without enhanced brightness found during stress imaging and during rest imaging is indicative of an infarct.

In one embodiment, the myocardial blood flow can be measured by (1) administering a first injection of a microparticle composition to a patient, (2) scanning the patient using an ultrasound machine imaging to obtain a visible image of the cardiovascular region, (3) inducing a state of stress in the patient using a pharmacological stressor or exercise, (4) administering a second injection of the microparticle composition and continuing the scanning, and (5) assessing differences in the images obtained in steps (2) and (4) either visually or using quantitative image analysis.

For radiology applications, the microparticles may be used to improve the capabilities of ultrasound imaging for radiology indications, including imaging of the kidney, liver and peripheral vascular disease, increasing the visibility of blood flow and blood flow patterns and by improving the detection of small lesions or structures deep within the body. The microparticles can be used for both macrovascular and microvascular indications. In macrovascular indications (the diagnosis of disease states and conditions of major arteries and veins of the body), the microparticles may aid in the detection of strokes and pre-stroke conditions through visualization of intracranial blood vessels, detecting atherosclerosis in large vessels such as the carotid arteries by assessing the degree of carotid artery stenosis, vascular graft patency and peripheral vascular thrombosis. For microvascular indications (the diagnosis of disease states and through analysis of patterns of small vessel blood flow), the microparticles may aid in identifying lesions, tumors or other diseases in the liver (e.g. adenomas or hemangiomas), kidneys, spleen (e.g. splenic artery aneurysms), breasts and ovaries and in other tissues and organs.

Diseased tissues in a patient may be diagnosed by administering the microparticle composition to the patient and scanning the patient using the ultrasound imaging to obtain visible images of any diseased tissues in the patient. Diseased tissues may manifest as a region of enhanced brightness or a region that does not show enhanced brightness.

Enhanced Images Obtained Using Microparticle Compositions

The microparticles produce an enhanced image following administration. Enhanced images may be manifested by an increase in brightness in the image compared to when no ultrasound contrast agent is administered or by substantial elimination of artifacts in the image. Thus, in connection with ultrasound imaging of the cardiovascular region, including the heart tissue and the vasculature associated therewith, an enhanced image may be manifested, for example, by increased brightness in the image of the cardiovascular region and/or a substantial elimination in the occurrence of artifacts in the image of the cardiovascular region. The images following a single administration of the agent last for between 10 seconds and 60 minutes. The images preferably last for between 20 seconds and 30 minutes and most preferably last for between 30 seconds and 20 minutes. In a preferred embodiment, the ultrasound imaging is enhanced in the ventricular chambers for more than five minutes or in the myocardium for more than one minute.

The increase in brightness in the image may be assessed either visually by the naked eye or using quantitative image analysis. With particular reference to the gray scale (about 0 to about 255 VDUs or gray levels) identified above, there is preferably an increase in the level of brightness of at least about 10 VDUs (gray levels). More preferably, the image has an increased brightness of greater than about 10 VDUs, for example, about 15, 20, 25, 30, 35, 40, 45, 50, 55, 60, 65, 70, 75, 80, 85, 90, 95, or 100 VDUs. In some embodiments, the increased brightness is greater than about 100 VDUs, for example, about 105, 110, 115, 120, 125, 130, 135, 140, 145, or 150 VDUs. In other embodiments, the increased brightness is greater than about 150 VDUs, for example, about 155, 160, 165, 170, 175, 18-, 185, 190, 195,or 200 VDUs. Alternatively, the increased brightness is greater than about 200 VDUs, for example about 205, 210, 215, 220, 225, 230, 235, 240, 245, 250, or 255 VDUs.

The methods and compositions described above will be further understood with reference to the following non-limiting examples.

EXAMPLES

Materials

Acetic acid, ammonium bicarbonate, mannitol USP, and polysorbate 80 (no animal-derived components) were purchased from Spectrum Chemicals, Gardena, Calif. Polymer (poly(lactide-co-glycolide) (PLGA) (50:50)) and diarachidoylphosphatidylcholine (1,2-diarachidoyl-sn-glycero-3-phosphocholine (DAPC)) were obtained from Boehringer Ingelheim (Ingelheim, Germany) and Avanti (Alabaster, Ala.), respectively. Methylene chloride was purchased from EM Science (EMD Chemicals, Gibbstown, N.J.). Vials (30 ml tubing vials) and stoppers (20 mm, gray, single-vent, Fluro-Tec) were obtained from West Pharmaceutical Services (Lionville, Pa.). n-Perfluorobutane (DFB) gas was purchased from F2 Chemicals Ltd, Lancashire, UK.

Analytical Methods

Quantitation of Mass Concentration of Microparticles

The mass concentration of microparticles in vials was quantitated using ICP-MS (inductively coupled plasma—mass spectrometry). The amount of polymer in the microparticles was determined by analyzing for tin by ICP-MS. The amount of polymer present in the microparticles was determined based on a comparison of the amount of tin found in the microparticles to the amount of tin found in the specific lot of polymer used to make the microparticles. The amount of phospholipid in the microparticles was determined by analyzing for phosphorus by ICP-MS. The amount of phosphorus present in the microparticles was determined based on the amount of phosphorous found in the microparticles in comparison to the amount of phosphorus in the phospholipid itself. The microparticle mass per mL of suspension was calculated by adding the amount of polymer and phospholipid per vial and then dividing that sum by the reconstitution volume (5 mL).

Particle Size Analysis

A sample of reconstituted microparticles was added to an electrolyte solution, and the resulting suspension analyzed for particle size and microparticle concentration using a Coulter Multisizer II fitted with a 50 µm aperture tube.

Gas Content of Microparticles

Vials of the dry powder were reconstituted with 5 mL water and shaken to create the microparticle suspension. The resulting suspension was analyzed for DFB content by withdrawing a set of 0.3 mL aliquots through the stopper using a needle and syringe. These aliquots were injected into sealed headspace vials. The headspace vials equilibrated for at least 10 hours at room temperature. Samples were then heated then heated to 45° C. for 20 minutes in a headspace sampler oven. The headspace gas above the suspension was analyzed by gas chromatography using a purged packed inlet and a flame ionization detector. Quantitation was performed using an area based single point calibration.

The GC system parameters and temperature program are listed in Tables 1 and 2.

TABLE 1

GC System Parameters

| | |
|---|---|
| Sampling: | Headspace, 1 mL sample loop |
| Detector: | FID |
| Column: | Supelco 60/80 Carbopack B 5% Fluorocol |

TABLE 1-continued

GC System Parameters

| Inlet Temperature: | 150° C. |
| --- | --- |
| Detector Temperature: | 325° C. |
| Carrier Gas: | Helium (25 mL/min) |
| FID Gases: | Hydrogen (60 mL/min) |
| | Air (350 mL/min) |
| | Nitrogen (5 mL/min) |

TABLE 2

GC Temperature Program

| | Initial Temp. | Rate | Final Temp. | Hold Time |
| --- | --- | --- | --- | --- |
| Initial Cond. | 40° C. | N/A | N/A | 2.0 min |
| First Ramp | 40° C. | 5° C./min | 65° C. | 0.0 min |
| Second Ramp | 65° C. | 10° C./min | 130° C. | 0.0 min |
| Third Ramp | 130° C. | 50° C./min | 200° C. | 0.0 min |
| Final Cond. | 200° C. | N/A | N/A | 3.1 min |

EXAMPLE 1

Production of Microparticles for Use as an Ultrasound Contrast Agent

An organic solution was prepared by dissolving 176 g of PLGA, 10.6 g of diarachidoylphosphatidylcholine (1,2-diarachidoyl-sn-glycero-3-phosphocholine (DAPC)), and 2.26 g of acetic acid in 5.88 L of methylene chloride at 25° C. An aqueous solution composed of 68.5 g of ammonium bicarbonate dissolved in 338 ml of water for injection was added to the organic solution and homogenized for 10 minutes at 4310 RPM in a 10 L homogenization tank using a rotor-stator emulsifying mixer.

The resulting emulsion was spray dried using nitrogen as both the atomizing and drying gas. Emulsions were spray dried on a bench top, spray dryer using an air-atomizing nozzle from Spraying Systems (Wheaton, Ill.) and a glass drying chamber/cyclone system from Buchi (Brinkmann, Westbury, N.Y.). Spray drying conditions were as follows: 40 ml/min emulsion flow rate, 30 L/min atomization gas rate, 46 kg/hr drying gas rate, and 12° C. outlet temperature.

The spray dried product was further processed through dispersion, freezing, and lyophilization steps. An aqueous vehicle was prepared by dissolving 140 g of mannitol and 4.10 g of polysorbate 80 in 5.0 L of water. The spray dried microparticles were dispersed in the vehicle at a concentration of 25 mg/ml. The dispersion was deaggregated using a stainless steel, 800 series, flow-cell sonicator from Misonix Incorporated (Farmingdale, N.Y.) and sieved through a 10" diameter vibratory sieve (RBF-10) from Vorti-Siv (Salem, Ohio). The sonicator was jacketed at 4° C. to prevent heating of the dispersion. The dispersion was sieved through 25 μm and 20 μm screens in series at 150 mL/min. The sieved dispersion was filled into vials (10 ml fill in 30 ml vials), partially stoppered, and frozen by immersion in liquid nitrogen.

Following freezing, the vials were lyophilized. At the conclusion of lyophilization, the chamber was isolated, and n-perfluorobutane (DFB) was backfilled into the vials to a pressure of −5 kilopascals prior to stoppering.

The dry powder was reconstituted with 5 mL of sterile water prior to use by adding the water to the vial of the dry powder and shaking to yield a suspension of microparticles in isosmotic mannitol. The suspension contained $2.2 \times 10^9$ microparticles/mL of suspension, and 37 mg microparticles/mL of suspension and the microparticles had a mean particle size of 2.2 microns.

EXAMPLE 2

Rate of Gas Leakage from the Microparticles

The rate of gas leakage from two separate batches (Batch 1 and Batch 2) of microparticles as produced by the methods of Example 1 was assessed using gas chromatography (GC) as described in the analytical methods sections. A third lot of microspheres (Batch 3) was produced similar to the method of example 1, however, the phospholipid, diarachidoylphosphatidylcholine (1,2-diarachidoyl-sn-glycero-3-phosphocholine (DAPC)) was omitted during the production of the microparticles.

TABLE 3

Gas Content and Rate of Gas Leakage for Microparticles

| | Gas Content (μg/mL suspension) Immediately Following Vial Reconstitution | Gas Content (μg/mL suspension) 70 minutes Following Vial Reconstitution | % Gas Content Lost over 70 minutes |
| --- | --- | --- | --- |
| Batch 1 | 341 | 312 | 9% |
| Batch 2 | 259 | 232 | 10% |
| Batch 3 | 139 | 18 | 87% |

The microparticles which contained DAPC lost approximately 10% of the starting gas content after 70 minutes whereas the microparticles which did not contain DAPC lost 87% of the starting gas content. Additionally, the microparticles which contained DAPC had a higher starting initial gas content relative to the microparticles without the DAPC. This indicates that the inclusion of DAPC is important to the formation of the internal porous structure of the microparticles during spray drying as well on retention of gas within the microparticles.

The total duration of intended use of an ultrasound contrast agent following administration to a subject is generally on the order of 30 seconds to 60 minutes depending on the type of cardiology or radiology ultrasound examination conducted. Thus gas loss from the microparticles containing the lipid DAPC is estimated to be insignificant over the period of the ultrasound examination

EXAMPLE 3

Cardiac Image Enhancement as a Function of Microparticle Dose

Microparticles as produced by the method in Example 1 were studied in healthy human adults. The dry powder was reconstituted prior to use by adding 5 mL of sterile water to the vial and shaking the vial ten times. The final concentration of microspheres in the resulting suspension was approximately 37 mg/mL. Subjects received a single dose of either 0.5 mg/kg, 2.0 mg/kg or 4.0 mg/kg body weight. Subjects underwent transthoracic ultrasound imaging using continuous harmonic imaging (frame rate 15 Hz and transducer frequency 2.1/4.2 MHz). Images were visually assessed for intensity and duration of enhancement.

The duration of enhancement in the ventricular chamber exceeded 9 minutes at both the 2 mg/kg and 4 mg/kg doses. The contrast effect was still apparent in 13 out of 15 of the subjects at these two doses when the subjects were re-imaged at 30 minutes, indicating the long duration of enhancement provided by the microparticles.

The duration of ventricular chamber enhancement is summarized in the Table 4.

TABLE 4

Duration of Left Ventricular Image Enhancement

| Dose (mg/kg body weight) | Mean Duration of Ventricular Chamber Enhancement (minutes) |
|---|---|
| 0.5 | 2.6 |
| 2.0 | >9.6 |
| 4.0 | >9.6 |

EXAMPLE 4

Comparison of Microparticles to Commercial Product for Assessing Cardiac Images

A comparative cardiac ultrasound imaging study was conducted in two adult men matched for body weight and cardiac function. The first subject received a single administration of microparticles as produced by the method of Example 1. The dry powder was reconstituted prior to use by adding 5 mL of sterile water to the vial and shaking the vial ten times. The final concentration of microspheres in the resulting suspension was approximately 37 mg/mL and the gas content of the suspension was approximately 250 µ/mL suspension. The first subject received a dose of 4 mg microparticle/kg which corresponds to a gas dose of 27 µg/kg body weight. The second subject received a single dose of the marketed ultrasound contrast agent, OPTISON® (Amersham Health) which contains perfluoropropane containing albumin microspheres. The two subjects received the same total amount of gas (27 µg/kg body weight) which is the acoustically active component. The two subjects underwent transthoracic ultrasound imaging using continuous harmonic imaging (frame rate 15 Hz and transducer frequency 2.1/4.2 MHz). Images were visually assessed for intensity and duration of enhancement.

The duration of ventricular chamber enhancement and myocardial enhancement is summarized in Table 5.

TABLE 5

Duration of Image Enhancement with Different Ultrasound Contrast Agents

| Contrast Agent and Dose of Gas Administered (µg/kg) | Duration of Ventricular Chamber Enhancement (minutes) | Duration of Myocardial Enhancement (seconds) |
|---|---|---|
| Example #1 Microparticles (27 µg/kg body weight) | >9 | 160 |
| OPTISON ® (27 µg/kg body weight) | 1 | 10 |

The microparticles produced using the method described in Example 1 provide enhanced images of both the ventricular chambers and the myocardium which are significantly longer than OPTISON® and which are of appropriate duration to conduct a complete cardiac exam by ultrasound.

EXAMPLE 5

Assessment of Myocardial Blood Flow to Assess Ischemia Using Microparticle Formulations Microparticles produced as per the method in Example 1 were administered to a subject being evaluated for coronary heart disease. The subject received two injections of the microparticles separated by 60 minutes. The first injection of the microparticles ("rest injection", 1.7 mg/kg) was used to assess the myocardium at rest. Prior to the second injection of the microparticles, the subject was pharmacologically stressed using the coronary vasodilator, dipyridamole (0.56 mg/kg). After the induction of stress, the subject received a second injection of the microparticles ("stress injection" 1.3 mg/kg) to assess the myocardium under stress.

The comparison of the rest and stress images over time post administration of the microparticles for the subject indicate a region of the myocardium which has minimal increase in image enhancement and this region becomes larger in size following the induction of the stress. This indicates the zone of myocardial tissue has both infarcted and ischemic components. The detection of ischemia was confirmed using an alternate diagnostic technique, nuclear imaging. Rest and stress nuclear perfusion were conducted following the administration of 99Tc (MIBI) and the subject was imaged using a commercial gamma counter. The defects noted on the ultrasound rest and stress images were confirmed on the rest and stress nuclear perfusion images.

We claim:

1. A method of evaluating myocardial blood flow in a patient by ultrasound comprising
    forming an isosmotic suspension comprising microspheres comprising a poly(hydroxy acid) or copolymer or blend thereof and a hydrophobic compound,
    wherein the microspheres are porous spheres with a honeycombed structure or sponge-like structure, and having incorporated therein a perfluorocarbon gas and a pharmaceutically acceptable carrier suitable for injection,
    wherein the suspension has a microsphere concentration ranging from $1.0 \times 10^9$ to $3.5 \times 10^9$ microspheres/mL of suspension or a microsphere mass concentration ranging from 25 to 50 mg microspheres/mL suspension,
    intravenously administering to the patient the suspension in a dose ranging from 0.5 to 4.0 mg microspheres/kg body weight, and
    imaging the patient's myocardium with ultrasound for more than one minute to produce an enhanced image of the myocardium for more than one minute compared to when no contrast agent is present.

2. The method of claim 1 further comprising administering to the patient an agent to stress the cardiovascular system of the patient and re-imaging the patient.

3. The method of claim 2, wherein the agent is selected from the group consisting of vasodilators, inotropic agents and chronotropic agents.

4. The method of claim 1, wherein the suspension has a microsphere concentration ranging from $1.5 \times 10^9$ to $2.8 \times 10^9$ microspheres/mL of suspension or a microsphere mass concentration ranging from 30 to 45 mg microspheres/mL suspension.

5. The method of claim 1, wherein the microspheres have a mean particle size of less than 8 microns.

6. The method of claim 5, wherein the microspheres have a mean particle size ranging from 1.9 to 2.6 microns.

7. The method of claim 1, wherein the dose is selected from the group consisting of 0.5 mg microspheres/kg body weight, 2.0 mg microspheres/kg body weight and 4.0 mg microspheres/kg body weight.

8. The method of claim 1, wherein the gas is selected from the group consisting of $CF_4$, $C_2F_4$, $C_2F_6$, $C_3F_6$, $C_3F_8$, $C_4F_8$, and $C_4F_{10}$.

9. The method of claim 8, wherein the gas is n-perfluorobutane ($C_4F_{10}$) provided in an amount between 75 and 500 mg/mL of reconstituted volume of suspension.

10. The method of claim 9 wherein the n-perfluorobutane ($C_4F_{10}$) is provided in an amount between 100 and 400 mg/mL of reconstituted volume of suspension.

11. The method of claim 10 wherein the n-perfluorobutane ($C_4F_{10}$) is provided in an amount between 150 and 350 mg/mL of reconstituted volume of suspension.

12. The method of claim 8 wherein the gas is n-octafluoropropane ($C_3F_8$) provided in an amount between 75 and 375 mg/mL of reconstituted volume of suspension.

13. The method of claim 12 wherein the n-octafluoropropane ($C_3F_8$) is provided in an amount between 120 and 300 mg/mL of reconstituted volume of suspension.

14. The method of claim 1, wherein the hydrophobic compound is incorporated with the poly(hydroxy acid), or copolymer or blend thereof ("polymer") at a ratio of between 1 and 12% (weight hydrophobic compound/weight polymer).

15. The method of claim 14, wherein the hydrophobic compound is a lipid.

16. The method of claim 15, wherein the lipid is a phospholipid selected from the group consisting of dioleoylphosphatidylcholine (DOPC), dimyristoylphosphatidylcholine (DMPC), dipentadecanoylphosphatidylcholine (DPDPC), dilauroylphosphatidylcholine (DLPC), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphosphatidylcholine (DLGPC), and phosphatidylethanolamines.

17. The method of claim 16, wherein the poly(hydroxy acid) copolymer is poly (lactide-co-glycolide) with a lactide to glycolide ratio of 1:1 and a weight average molecular weight ranging from 20 to 40 kDa, and wherein the lipid is diarachidoylphosphatidylcholine incorporated with the polymer in a range of between 5 and 6.6% (weight lipid/weight poly(hydroxy acid) copolymer).

18. The method of claim 1, wherein the suspension further comprises one or more excipients selected from the group consisting sugars, salts, and surfactants.

19. The method of claim 1, wherein the poly(hydroxy acid) copolymer is poly (lactide-co-glycolide), wherein the hydrophobic compound is diarachidoylphosphatidylcholine, and wherein the gas is n-perfluorobutane ($C_4F_{10}$).

* * * * *

UNITED STATES PATENT AND TRADEMARK OFFICE
CERTIFICATE OF CORRECTION

| | | |
|---|---|---|
| PATENT NO. | : 8,012,457 B2 | Page 1 of 1 |
| APPLICATION NO. | : 11/143170 | |
| DATED | : September 6, 2011 | |
| INVENTOR(S) | : Richard Walovitch et al. | |

It is certified that error appears in the above-identified patent and that said Letters Patent is hereby corrected as shown below:

In claim 18, column 22, line 22, replace "consisting sugars" with --consisting of sugars--.

Signed and Sealed this
Twenty-eighth Day of February, 2012

David J. Kappos
*Director of the United States Patent and Trademark Office*